(12) United States Patent
Cotton

(10) Patent No.: US 7,622,552 B2
(45) Date of Patent: Nov. 24, 2009

(54) LIGATION METHOD

(75) Inventor: Graham Cotton, Edinburgh (GB)

(73) Assignee: Almac Sciences (Scotland) Limited, Edinburgh (GB)

(*) Notice: Subject to any disclaimer, the term of this patent is extended or adjusted under 35 U.S.C. 154(b) by 0 days.

(21) Appl. No.: 10/567,403

(22) PCT Filed: Aug. 5, 2004

(86) PCT No.: PCT/GB2004/003391

§ 371 (c)(1),
(2), (4) Date: Mar. 30, 2006

(87) PCT Pub. No.: WO2005/014620

PCT Pub. Date: Feb. 17, 2005

(65) Prior Publication Data

US 2006/0247417 A1      Nov. 2, 2006

(30) Foreign Application Priority Data

Aug. 5, 2003   (GB)   ................................... 0318276.3
Aug. 28, 2003  (GB)   ................................... 0320122.5

(51) Int. Cl.
*C07K 1/08*    (2006.01)
*C07K 1/107*   (2006.01)
*C07K 2/00*    (2006.01)

(52) U.S. Cl. ................... 530/339; 530/300; 530/323; 530/333; 530/345; 530/402; 530/409; 530/410

(58) Field of Classification Search ....................... None
See application file for complete search history.

(56) References Cited

U.S. PATENT DOCUMENTS 3,985,617 A * 10/1976 Yugari et al. ................. 435/176
5,965,714 A * 10/1999 Ryall .......................... 530/402
6,194,451 B1 * 2/2001 Alpegiani et al. ........... 514/459

(Continued)

FOREIGN PATENT DOCUMENTS

WO      WO 00/18881 A1    4/2000

OTHER PUBLICATIONS

Bonnet et al. Chemoselective acylation of hydrazinopeptides . . . Tetrahedron Letters. 2000, vol. 41, pp. 45-48.*

(Continued)

*Primary Examiner*—Jeffrey E Russel
(74) *Attorney, Agent, or Firm*—Daniel A. Monaco; Drinker Biddle & Reath LLP

(57) ABSTRACT

A method of ligating two or more molecules, for example, peptides to peptides or peptides to labels is provided. The method may comprise the steps: a) providing a first oligopeptide having a reactive moiety, which is a hydrazine moiety, a hydrazide moiety or an amino-óxy moiety b) providing a second oligopeptide having an activated ester moiety, c)allowing the reactive moiety of the first oligopeptide to react with the activated ester moiety of the second oligopeptide to form an oligopeptide product, in which the first and second oligopeptides are linked via a linking moiety having Formula I, II or III. The second oligopeptide may preferably be generated by thiol reagent induced cleavage of an intein fusion protein. The invention further provides labelling and ligation methods in which protein hydrazides are ligated by reaction of the hydrazide moiety with an aldehyde functionality or a ketone functionality.

20 Claims, 15 Drawing Sheets

Ligation of protein and peptide thioesters with hydrazine and aminooxy containing entities such as labels, peptides and proteins.

U.S. PATENT DOCUMENTS

2004/0058390 A1* 3/2004 Nock et al. .................. 435/7.1
2004/0067537 A1* 4/2004 Hahn et al. .................. 435/7.2

OTHER PUBLICATIONS

Vanderesse et al. Alpha-Aminoxy Acids as Building Blocks for the Oxime . . . Journal of Peptide Science. May 2003, vol. 9, Issue 5, pp. 282-299.*

Salvadori et al. Aminoxy Analogs of Leu-Enkephalin. International Journal of Peptide and Protein Research. 1981, vol. 18, pp. 393-401.*

Perler et al., "The mechanism of protein splicing: variations on a theme", *Peptides 2002*, pp. 254-255 (2002).

Chong et al., "Single-column purification of free recombinant proteins using a self-cleavable affinity tag derived from a protein splicing element", *Gene: An International Journal on Genes and Genomes* 192(2):271-281 (1997).

Cotton et al., "Peptide ligation and its application to protein engineering", *Chemistry and Biology* 6(2):R247-R256 (1999).

Geoghegan, K F, "Site-directed conjugation of nonpeptide groups to peptides and proteins via periodate oxidation of a 2-amino alcohol. Application to modification at N-terminal serine", *Bioconjugate Chemistry, American Chemical Society* 3(2):138-146 (1992).

* cited by examiner

Figure 1 General principle of chemical ligation.

Figure 2 Mechanism of protein splicing

Figure 3 Generation of Recombinant C-terminal Thioester Proteins

Figure 4 Ligation of protein and peptide thioesters with hydrazine and aminooxy containing entities such as labels, peptides and proteins.

Figure 5 Generation of synthetic and recombinant peptide hydrazides for ligation with thioester containing molecules Figure 6 Generation of recombinant peptide hydrazides for ligation with aldehyde and ketone containing molecules Figure 9. ESMS spectrum of the C-terminal hydrazide derivative of Grb2-SH2

Figure 10. SDS-PAGE analysis of the reaction between synthetic ketone containing peptide CH3COCO-myc with Grb2-SH2 – C-terminal hydrazide and Cytochrome C.

Figure 11 Structure of CH₃COCO-Lys(Fl).

LIGATION METHOD

FIELD OF THE INVENTION

This application relates to a method of ligating two, or more molecules, for example, small organic molecules, labels, peptides etc. In particular it relates to a method of ligating a peptide, such as ligation of a synthetic peptide to a recombinant peptide.

BACKGROUND TO THE INVENTION

Protein engineering methodologies have proven to be invaluable for generating protein based tools for application in basic research, diagnostics, drug discovery and as protein therapeutics. The ability to manipulate the primary structure of a protein in a controlled manner opens up many new possibilities in the biological and medical sciences. As a consequence, there is a concerted effort on developing methodologies for the site-specific modification of proteins and their subsequent application.

The two main approaches to generating proteins are through recombinant methods or chemical synthesis. To date, the two methods have proved to be complementary; recombinant methodologies enable proteins of any size to be generated but in general they are restricted to the assembly of the proteinogenic amino acids. Thus, in general, the introduction of labels and probes into recombinant proteins has to be implemented post-translationally and does not allow modifications to the protein backbone.

The most common methods for labelling a recombinant protein use an amino or a thiol reactive version of the label that will covalently react with a lysine side chain/$N^\alpha$ amino group or a cysteine side chain within the protein respectively. For such labelling methods to be site-specific, an appropriate derivative of the protein must be engineered to contain a unique reactive functionality at the position to be modified. This requires all the other naturally occurring reactive functionalities within the primary sequence to be removed through amino acid mutagenesis. In the case of protein amino functionalities, this is essentially impossible due to the abundance of lysine residues within proteins and the presence of the amino functionality at the N-terminus of the sequence. Likewise, for cysteine this process is laborious and is often detrimental to the function of the protein.

The production of proteins having site-specific modifications and/or labels is more readily achievable using chemical synthesis methods. The chemical synthesis of proteins enables multiple modifications to be incorporated into both side-chain and backbone moieties of the protein in a site-specific manner, but, in general, the maximum size of sequence that can be synthesised and isolated is circa 50-100 amino acids.

Protein Ligation

A further approach to the generation of proteins is protein/peptide ligation. In this approach mutually reactive chemical functionalities (orthogonal to the chemistry of the naturally occurring amino acids i.e. which react by mutually exclusive chemistries compared to the reactions of the reactive moieties of the naturally occuring amino acids) are incorporated at the N- and C-termini of unprotected polypeptide fragments such that when they are mixed, they react in a chemoselective manner to join the two sequences together (Cotton G J and Muir T W. Chem. Biol., 1999, 6, R247-R254). The principle of chemical ligation is shown schematically in FIG. 1.

A number of chemistries have been utilised for the ligation of two synthetic peptides where a diverse range of different chemical functionalities can be incorporated into the termini of polypeptides using solid phase peptide synthesis. These include the reaction between a thioacid and bromo-alkyl to form a thioester (Schnolzer M and Kent S B H, Science, 1992, 256, 221-225), reaction of an aldehyde with an N-terminal cysteine or threonine to form thiazolidine or oxazolidine respectively (Liu C-F and Tam J P. Proc. Natl. Acad. Sci. USA, 1994, 91, 6584-6588), reaction between a hydrazide and an aldehyde to form a hydrazone (Gaertner H F et al, et al Bioconj. Chem., 1992, 3, 262-268) reaction of an aminoxy group and an aldehyde to form an oxime (Rose K. *J. Am. Chem. Soc.,* 1994, 116, 30-33), reaction of azides and aryl phosphines to form an amide bond (Staudinger ligation) (Nilsson B L, Kiessling L L, and Raines R T. *Org. Lett.,* 2001, 3, 9-12, Kiick et al *Proc. Natl. Acad. Sci.* USA, 2002, 99, 19-24), and the reaction of a peptide C-terminal thioester and an N-terminal cysteine peptide to form a native amide bond (Dawson et al. *Science,* 1994, 266, 776) (Native chemical ligation U.S. Pat. No. 6,184,344, EP 0832 096 B1). This native chemical ligation method is an extension of studies by Wieland and coworkers who showed that the reaction of ValSPh and CysOH in aqueous buffer yielded the dipeptide ValCysOH (Wieland T et al,. Liebigs Ann. Chem., 1953, 583, 129-149).

Although the native chemical ligation method has proved popular, it requires an N-terminal cysteine containing peptide for the reaction and thus, if a cysteine is not present at the appropriate position in the protein, a cysteine needs to be introduced at the ligation site. However, the introduction of extra thiol groups into a protein sequence may be detrimental to its structure/function, especially since cysteine has a propensity to form disulfide bonds which may disrupt the folding pathway or compromise the function of the folded protein.

As a consequence of the difficulties and problems associated with known ligation techniques, the ligation of two synthetic fragments generally only enables proteins of circa 100-150 amino acids to be chemically synthesised. Although larger proteins have been synthesised by ligating together more than two fragments, this has proved to be technically difficult (Camarero et al. *J. Pept. Res.,* 1998, 54, 303-316, Canne L E et al, *J. Am. Chem. Soc.,* 1999, 121, 8720-8727).

Protein Semi-Synthesis

Protein ligation technologies that enable both synthetic and recombinantly derived protein fragments to be joined together have been described. This enables large proteins to be constructed from combinations of synthetic and recombinant fragments, allowing proteins to be site-specifically modified with both natural and unnatural entities. By utilising such so-called protein semi-synthesis, many different synthetic moieties can be site-specifically incorporated at multiple different sites within a target protein.

In order to utilise recombinant proteins in ligation strategies the recombinant fragments must contain the appropriate reactive functionalities to facilitate ligation. One approach to introduce a unique reactive functionality into a recombinant protein has been through the periodate oxidation of N-terminal serine containing sequences. Such treatment converts the N-terminal serine into a glyoxyl moiety, which contains an N-terminal aldehyde. Synthetic hydrazide containing peptides have then been ligated to the N-terminus of these proteins in a chemoselective manner through hydrazone bond formation with the protein N-terminal glyoxyl group (Gaertner H F et al, et al Bioconj. Chem., 1992, 3, 262-268, Gaertner H F, et al. *J. Biol. Chem.,* 1994, 269, 7224-7230). Another approach has been to generate recombinant proteins with N-terminal cysteine residues. Synthetic peptides containing C-terminal thioesters have then been site-specifically attached to the N-terminus of these proteins via amide bond formation in a manner analogous to 'native chemical ligation' (Cotton G J and Muir T W. *Chem. Biol.*, 2000, 7, 253-261). However as with the ligation of synthetic peptides using native chemical ligation techniques, the technology requires a cysteine to be introduced at the ligation site if the primary sequence does not contain one at the appropriate position.

Protein Splicing Techniques

Recently technologies have been developed which enable recombinant proteins containing C-terminal thioester groups to be generated. The C-terminal thioester functionality provides a unique reactive chemical group within the protein that can be utilised for protein ligation. Recombinant C-terminal thioester proteins are produced by manipulating a naturally occurring biological phenomenon known as protein splicing (Paulus H. *Annu Rev Biochem* 2000, 69, 447-496). Protein splicing is a post-translational process in which a precursor protein undergoes a series of intramolecular rearrangements which result in precise removal of an internal region, referred to as an intein, and ligation of the two flanking sequences, termed exteins (FIG. 2). While there are generally no sequence requirements in either of the exteins, inteins are characterised by several conserved sequence motifs and well over a hundred members of this protein domain family have now been identified.

The first step in protein splicing involves an N→S (or N→O) acyl shift in which the N-extein unit is transferred to the sidechain SH or OH group of a conserved Cys/Ser/Thr residue, always located at the immediate N-terminus of the intein. Insights into this mechanism have led to the design of a number of mutant inteins which can only promote the first step of protein splicing (Chong et al *Gene*. 1997, 192, 271-281, (Noren et al., *Angew. Chem. Int. Ed. Engl.*, 2000, 39, 450-466). Proteins expressed as in frame N-terminal fusions to one of these engineered inteins can be cleaved by thiols via an intermolecular transthioesterification reaction, to generate the recombinant protein C-terminal thioester derivative (FIG. 3) (Chong et al *Gene*. 1997, 192, 271-281, (Noren et al., *Angew. Chem. Int. Ed. Engl.*, 2000, 39, 450-466) (New England Biolabs Impact System WO 00/18881, WO 0047751). Peptide sequences containing an N-terminal cysteine residue can then be specifically ligated to the C-termini of such recombinant C-terminal thioester proteins (Muir et al *Proc. Natl. Acad. Sci. USA.*, 1998, 95, 6705-6710, Evans Jr et al. *Prot. Sci.*, 1998, 7, 2256-2264), in a procedure termed expressed protein ligation (EPL) or intein-mediated protein ligation (IPL).

The chemoselective ligation of N-terminal cysteine containing peptides to C-terminal thioester containing peptides, be they synthetic or recombinant, is performed typically at slightly basic pH and in the presence of a thiol cofactor. The strategy also requires a cysteine to be introduced at the ligation site, if one is not suitably positioned within the primary sequence. These requirements of this ligation approach have the potential to alter the structure and/or function of both the protein ligation product and the initial reactants.

For example, the chemokine RANTES is unstable in a buffer of 100 mM NaCl, 100 mM sodium phosphate pH 7.4 containing 100 mM 2-mercaptoethanesulfonic acid (MESNA); a buffer typically used for the ligation of C-terminal thioester molecules to N-terminal cysteine containing molecules (expressed protein ligation and native chemical ligation). RANTES contains two disulphide bonds critical for maintaining the structure and function of the protein. In the typical ligation buffer described above, the folded protein was found to be converted within 48 hours to a mixture of the reduced protein and MESNA protein adducts. The majority of the protein mixture subsequently formed a precipitate, presumably reflecting the unfolded nature of these species (Cotton, unpublished).

Accordingly, the inventors believe that ligation reactions that require thiol containing buffers are, in general, not suitable for maintaining the integrity of disulphide bond containing proteins, such as antibodies, antibody fragments and antibody domains, cytokines, growth factors etc. Thus there is a requirement for ligation approaches that are typically performed in the absence of thiols. For example, when monitored over a number of days, it was found that RANTES was stable in 100 mM NaCl, 100 mM sodium phosphate buffer pH 7.4 and 100 mM sodium acetate buffer pH 4.5 (inventor's unpublished results). Ligation reactions that can be performed under such conditions should therefore be applicable for both disulphide and non-disulphide containing proteins.

Protein Labelling

Historically protein ligation means the joining together of two peptide/protein fragments but this is synonymous with protein labelling whereby the label is a peptide or derivatised peptide. Equally if a small non-peptidic synthetic molecule contains the necessary reactive chemical functionality for protein ligation, then ligation of the synthetic molecule directly to either the N- or C-termini of the protein affords site-specific labelling of the protein. Thus technologies developed for the ligation of protein fragments can also be used for the direct labelling of either the N- or C-termini of peptides or proteins in a site-specific manner irrespective of their sequence.

Recombinant proteins containing N-terminal glyoxyl functions (generated through periodate oxidation of the corresponding N-terminal serine protein) have been site-specific N-terminally labelled through reaction with hydrazide or aminoxy derivatives of the label (Geoghegan K F and Stroh J G. *Bioconj Chem.*, 1992, 3, 138-146, Alouni S et al. *Eur. J. Biochem.*, 1995, 227, 328-334). Also recombinant proteins containing N-terminal cysteine residues have been N-terminally labelled through reaction with labels containing thioester functionalities, the label being the acyl substituent of the thioester (Schuler B and Pannell L K. *Bioconjug. Chem.*, 2002, 13, 1039-43) and aldehyde functionalities (Zhao et al. *Bioconj. Chem.*, 1999, 10, 424-430) to form amides and thiazolidines respectively.

Though a number of methods for ligation of proteins exist each one has its potential drawbacks. There is thus a need for novel ligation methodologies, especially those that are compatible with both synthetic and recombinant fragments, and which may be used in the ligation of disulphide bond containing proteins as well as non disulphide bond containing proteins, which will complement the existing technologies and add another string to the protein engineer's bow.

SUMMARY OF THE INVENTION

The present inventors have overcome a number of problems associated with the prior art and have developed a new method for ligating peptide molecules which overcomes a number of the problems of the prior art.

Accordingly, in a first aspect of the present invention, there is provided a method of producing an oligopeptide product, the method comprising the steps:

a) providing a first oligopeptide, the first oligopeptide having a reactive moiety,
b) providing a second oligopeptide, the second oligopeptide having an activated ester moiety
c) allowing the reactive moiety of the first oligopeptide to react with the activated ester moiety of the second oligopeptide to form an oligopeptide product, in which the first and second oligopeptides are linked via a linking moiety having Formula I, Formula II or Formula III.

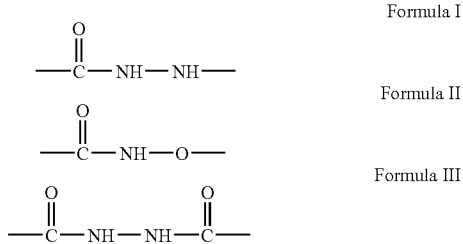

In preferred embodiments, in step (c), where said oligopeptides are linked via a linking moiety having Formula II and where said activated ester moiety of step (b) is not a thioester, said activated ester is a terminal activated ester moiety.

In further preferred embodiments of the invention, said linking moieties are linked via a linking moiety having Formula I or Formula III.

Unless the context demands otherwise, the terms peptide, oligopeptide, polypeptide and protein are used interchangeably.

The activated ester moiety of the first oligopeptide may be any suitable activated ester moiety, such as a thioester moiety, a phenolic ester moiety, an hydroxysuccinimide moiety, or an O-acylisourea moiety.

In preferred embodiments of the invention, the activated ester moiety is a thioester moiety. Any suitable thioester peptides wherein the peptide is the acyl substituent of the thioester may be used in the present invention (FIG. 4).

Such thioester peptides may be synthetically or recombinantly produced. The skilled person is well aware of methods known in the art for generating synthetic peptide thioesters. For example, synthetic peptide thioesters may be produced via synthesis on a resin that generates a C-terminal thioester upon H F cleavage (Hojo et al, Bull. Chem. Soc. Jpn., 1993, 66, 2700-2706). Further, the use of 'safety catch' linkers has proved to be popular for generating C-terminal thioesters through thiol induced resin cleavage of the assembled peptide (Shin Y et al, J. Am. Chem. Soc., 1999, 121, 11684-11689).

Moreover, recently technologies have been developed which enable recombinant C-terminal thioester proteins to be generated. Recombinant C-terminal thioester proteins may be produced by manipulating a naturally occurring biological phenomenon known as protein splicing. As described above, protein splicing is a post-translational process in which a precursor protein undergoes a series of intramolecular rearrangements which result in precise removal of an internal region, referred to as an intein, and ligation of the two flanking sequences, termed exteins.

As described above, a number of mutant inteins which can only promote the first step of protein splicing have been designed (Chong et al Gene. 1997, 192, 271-281, Noren et al., Angew. Chem. Int. Ed. Engl., 2000, 39, 450-466). Proteins expressed as in frame N-terminal fusions to one of these engineered inteins can be cleaved by thiols via an intermolecular transthioesterification reaction, to generate the recombinant protein C-terminal thioester derivative (Chong et al Gene. 1997, 192, 271-281, Noren et al., Angew. Chem. Int. Ed. Engl., 2000, 39, 450-466) (New England Biolabs Impact System WO 00/18881, WO 0047751). Such protein thioesters may be used in the methods of the invention (See FIG. 3).

Accordingly, in a preferred aspect of the present invention, in step (b), the second oligopeptide is generated by thiol reagent induced cleavage of an intein fusion protein.

Accordingly, in a second aspect of the present invention, there is provided a method of producing an oligopeptide product, the method comprising the steps:
a) providing a first oligopeptide, the first oligopeptide having a reactive moiety,
b) (i) providing a precursor oligopeptide molecule, the precursor oligopeptide molecule comprising a precursor second oligopeptide fused N-terminally to an intein domain
(ii) allowing thiol reagent dependent cleavage of the precursor molecule to generate a second oligopeptide molecule, said second oligopeptide molecule having a thioester moiety at its C-terminus
c) allowing the reactive moiety of the first oligopeptide to react with the second oligopeptide molecule to form an oligopeptide product, in which the first and second oligopeptides are linked via a linking moiety having Formula I, II or III.

The reactive moiety of the first oligopeptide may be any suitable reactive moiety. In preferred embodiments of the invention, the reactive moiety is a hydrazine moiety, an amino-oxy moiety or a hydrazide moiety having general formula IV, V or VI respectively.

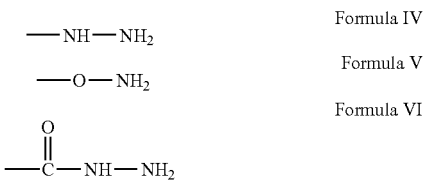

For example, in a particular preferred embodiment, the reactive moiety has Formula IV and, in the oligopeptide product produced by the method of the invention, the first and second oligopeptides are linked via a linking moiety having Formula I.

In a further preferred embodiment, the reactive moiety has Formula V and, in the oligopeptide product produced by the method of the invention, the first and second oligopeptides are linked via a linking moiety having Formula II.

In another preferred embodiment, the reactive moiety has Formula VI and, in the oligopeptide product produced by the method of the invention, the first and second oligopeptides are linked via a linking moiety having Formula III.

As described above, the first oligopeptide comprises a reactive moiety, which, in preferred embodiments, may be a hydrazine moiety (e.g. Formula IV), an amino-oxy moiety (e.g. Formula V) or an hydrazide moiety (e.g. Formula VI).

A particular advantage of the ligation method of the invention is that it may be performed in the absence of thiols. This enables efficient ligation of proteins/peptides comprising disulphide bonds as well as of proteins without such bonds.

Accordingly, in an embodiment of the first and second aspects of the invention, at least one of the first and second oligopeptides comprises one or more disulphide bonds.

Hydrazine, hydrazide or aminooxy containing derivatives of synthetic oligopeptides may be readily produced using known methods, for example, solid phase synthesis techniques.

Further, the present inventors have also found that proteins fused N-terminal to an intein domain can be cleaved from the intein by hydrazine treatment in a selective manner to liberate the desired protein as its corresponding hydrazide derivative (for example, see FIG. 5).

Accordingly, in further preferred embodiments of the invention, the first oligopeptide is generated by reaction of hydrazine with an oligopeptide molecule comprising the first oligopeptide fused N-terminal to an intein domain.

Indeed the discovery that such protein hydrazides may be produced by means of such a reaction forms an independent aspect of the present invention.

Accordingly, a third aspect of the invention provides a method of generating a protein hydrazide, said method comprising the steps:
(a) providing an protein molecule comprising an oligopeptide fused N-terminal to an intein domain,
(b) reacting said protein molecule with hydrazine, such that the intein domain is cleaved from the oligopeptide to generate a protein hydrazide.

Moreover, as well as using such a reaction to generate a first oligopeptide having a hydrazide moiety at its C-terminal, the first oligopeptide thus being available for reaction with the second oligopeptide having the activated ester moiety, the present invention further extends to a "one-step" process for ligating two peptides to generate an oligopeptide product.

This may be achieved by reacting a suitable protein linked N-terminal to an intein directly with a polypeptide having a hydrazine, hydrazide or amino-oxy moiety.

Accordingly, in a fourth aspect, the invention provides a method of producing an oligopeptide product, the method comprising the steps:
a) providing a first oligopeptide, the first oligopeptide having a reactive moiety, wherein the reactive moiety is a hydrazine moiety, a hydrazide moiety or an amino-oxy moiety;
(i) providing a precursor oligopeptide molecule, the precursor oligopeptide molecule comprising a second oligopeptide fused N-terminally to an intein domain;
(c) allowing the reactive moiety of the first oligopeptide to react with the precursor oligopeptide molecule to form an oligopeptide product, in which the first and second oligopeptides are linked via a linking moiety having Formula I, Formula II or Formula III.

The ligation technology of the present invention can thus utilise both synthetic and recombinant proteins and peptides. It thus enables the ligation of two or more synthetic peptides, the ligation of two or more recombinant peptides or the ligation of at least one synthetic peptide with at least one recombinant peptide.

Moreover, as well as providing a novel method of ligating peptides, the present invention may be used for the labelling of synthetic or recombinant peptides.

Accordingly, in a fifth aspect of the present invention, there is provided a method of labelling an oligopeptide, the method comprising the steps:
a) providing a label molecule, the label molecule having a reactive moiety,
b) providing the oligopeptide, the oligopeptide having an activated ester moiety
c) allowing the reactive moiety of the label molecule to react with the activated ester moiety of the oligopeptide to form the labelled oligopeptide, in which the label molecule and the oligopeptide are linked via a linking moiety having Formula I, Formula II or Formula III as defined above, In preferred embodiments, in step (c), where said label molecule and the oligopeptide are linked via a linking moiety having Formula II and where said activated ester moiety of step (b) is not a thioester, said activated ester is a terminal activated ester moiety.

In a preferred aspect of the present invention, in step (b) the oligopeptide is generated by thiol induced cleavage of an intein fusion protein.

Accordingly, in a sixth aspect of the present invention, there is provided a method of labelling an oligopeptide, the method comprising the steps:
a) providing a label molecule, the label molecule having a reactive moiety,
c) (i) providing a precursor oligopeptide molecule, the precursor oligopeptide molecule comprising a precursor oligopeptide fused N-terminally to an intein domain
(ii) allowing thiol reagent dependent cleavage of the precursor molecule to generate an oligopeptide molecule, said oligopeptide molecule having a thioester moiety at its C-terminus
c) allowing the reactive moiety of the label molecule to react with the oligopeptide to form the labelled oligopeptide, in which the label molecule and the oligopeptide are linked via a linking moiety having Formula I, II or III.

Alternatively, a label molecule having a terminal activated ester moiety may be used to label an oligopeptide having a reactive moiety. Thus, in a seventh aspect of the invention, there is provided a method of labelling an oligopeptide, the method comprising the steps:
a) providing a label molecule, the label molecule having an activated ester moiety of which the label is the acyl substituent,
b) providing the oligopeptide, the oligopeptide having a reactive moiety
c) allowing the activated ester moiety of the label molecule to react with the reactive moiety of the oligopeptide to form the labelled oligopeptide, in which the label molecule and the oligopeptide are linked via a linking moiety having Formula I, Formula II or Formula III
wherein, in step (c), where said label molecule and the oligopeptide are linked via a linking moiety having Formula II and where said activated ester moiety of step (b) is not a thioester, said activated ester is a terminal activated ester moiety.

As with the ligation technology, an oligopeptide present as a precursor molecule linked to an intein molecule may be labelled directly. Thus, an eighth aspect of the present invention provides a method of labelling an oligopeptide, the method comprising the steps:
a) providing a label molecule, the label molecule having a reactive moiety,
b) providing a precursor oligopeptide molecule, the precursor oligopeptide molecule comprising an oligopeptide fused N-terminally to an intein domain,
c) allowing the reactive moiety of the label molecule to react with the precursor oligopeptide molecule to form a labelled oligopeptide product, in which the label molecule and the oligopeptide are linked via a linking moiety having Formula I, Formula II or Formula III as defined above.

Any suitable label molecule known to the skilled person may be used in methods of the invention. The choice of label will depend on the use to which the labelled peptide is to be put. For example labels which may be used in the methods of the invention may include fluorophores, crosslinking reagents, spin labels, affinity probes, imaging reagents, for example radioisotopes, chelating agents such as DOTA, polymers such as PEG, lipids, sugars, cytotxic agents, and solid surfaces and beads.

In particular embodiments of the fifth, sixth, and seventh aspects of the invention, at least one of the label and oligopeptides comprises one or more disulphide bonds.

The methods of the invention are particularly useful in the ligation of peptides, in particular the ligation of peptides, which, using conventional ligation techniques, would require various protecting groups. The inventors have shown that the methods of the invention may be performed under pH conditions in which only the reactive moieties will react.

In preferred embodiments of the first and second and in preferred embodiments of the fourth to eighth aspects of the invention, step (c) of the method is performed at a pH in the range pH 4.0 to pH 8.5, preferably pH 4.0 to 8.0, for example, pH 4.0 to 7.5, more preferably in the range pH 5.0 to pH 8.0, more preferably in the range pH 6.0 to pH 7.5, most preferably in the range pH 6.5 to pH 7.5.

For example, the inventors have demonstrated that synthetic peptide C-terminal thioesters specifically react with hydrazine under aqueous conditions at pH 6.0 to form the corresponding peptide hydrazide. This allows ligation methods as described herein to be performed at pH 6.0, without the need for a potentially harmful thiol cofactor (useful if either fragment or final construct is thiol sensitive) and does not lead to the introduction of potentially reactive side-chain groups (such as a thiol) into the protein. Similarly, the inventors have demonstrated that synthetic peptide C-terminal thioesters specifically react with hydroxylamine under aqueous conditions at pH 6.0 and pH 6.8 to form the corresponding peptide hydroxamic acid. In addition, as described below, the inventors have demonstrated that both synthetic peptide C-terminal thioesters and recombinant protein C-terminal thioesters specifically react with O-methylhydroxylamine under aqueous conditions at pH 7.5, to form the corresponding C-terminal N-methoxy amide derivatives. This allows ligation methods as described herein to be performed at pH 7.5, without the need for a potentially harmful thiol cofactor.

Peptides and proteins that contain thioester groups (where the peptide is the acyl substituent of the thioester) can be reacted with hydrazine, hydrazide or aminooxy derivatives of a label or a peptide to afford site-specific labelling and chemoselective ligation respectively (see, for example, FIGS. 4 and 5).

In an analogous fashion, peptides that contain hydrazine, hydrazide or aminooxy groups can be reacted with thioester derivatives of a label or a peptide to afford site-specific labelling and chemoselective ligation respectively (see, for example, FIGS. 4 and 5).

Furthermore, having demonstrated that recombinant protein hydrazides can be generated by cleavage of protein-intein fusions with hydrazine, the inventors have shown that such protein hydrazides may be ligated by reaction of the hydrazide moiety with reactive groups other than activated ester moieties, for example an aldehyde functionality or a ketone functionality. For example, as described below, the inventors have shown that a pyruvoyl derivative of a synthetic peptide can be chemoselectively ligated to the C-terminus of recombinant protein hydrazides using the described approach, and in an analogous fashion, a pyruvoyl derivative of fluorescein was used to site-specifically label the C-terminus of recombinant protein hydrazides using the described approach.

This aspect of the invention provides a further novel method of ligating a recombinant peptide to a second peptide or indeed a label.

Thus, a ninth aspect of the invention provides a method of producing an oligopeptide product, the method comprising the steps:
a) providing a first oligopeptide, the first oligopeptide having an aldehyde or ketone moiety,
b) providing a precursor oligopeptide molecule, the precursor oligopeptide molecule comprising a second oligopeptide fused N-terminally to an intein domain,
c) reacting said precursor oligopeptide molecule with hydrazine to generate an oligopeptide molecule comprising an intermediate oligopeptide, said intermediate oligopeptide having a C-terminal hydrazide moiety,
d) allowing the aldehyde or ketone moiety of the first oligopeptide to react with the hydrazide moiety of the intermediate oligopeptide molecule to form an oligopeptide product, in which first oligopeptide and the second oligopeptide are linked via a hydrazone linking moiety.

An example of this aspect is shown in FIG. 6.

A tenth aspect of the invention provides a method of labelling an oligopeptide, the method comprising the steps:
a) providing a label molecule, the label molecule having a aldehyde or ketone moiety,
b) providing a precursor oligopeptide molecule, the precursor oligopeptide molecule comprising a first oligopeptide fused N-terminally to an intein domain,
c) reacting said precursor oligopeptide molecule with hydrazine to generate an oligopeptide molecule comprising an intermediate oligopeptide, said intermediate oligopeptide having a terminal hydrazide moiety,
d) allowing the aldehyde or ketone moiety of the label molecule to react with the hydrazide moiety of the intermediate oligopeptide molecule to form a labelled oligopeptide product, in which the label molecule and oligopeptide are linked via a hydrazone linking moiety.

In preferred embodiments of the ninth and tenth aspects of the invention, the hydrazone moiety has Formula VII:

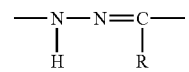

where R is H or any substituted or unsubstituted, preferably unsubstituted, alkyl group.

In preferred aspects of the ninth and tenth aspects of the invention, the method is performed at a pH in the range pH 1.0 to pH 7.0, preferably pH 1.0 to pH 6.0, more preferably in the range pH 2.0 to pH 5.5, most preferably in the range pH 2.0 to pH 4.5.

In a particular embodiment of the ninth and tenth aspects of the invention, the aldehyde or ketone containing moiety of the oligopeptide or of the label is an α-diketone group or an α-keto aldehyde group.

In a eleventh aspect of the present invention, there is provided an oligopeptide product produced using a method of the invention.

In an twelfth aspect, there is provided a labelled oligopeptide comprising an oligopeptide labelled according to a method of the invention.

Preferred features of each aspect of the invention are as for each of the other aspects mutatis mutandis.

The invention will now be described further in the following non-limiting examples with reference made to the accompanying drawings in which.

Figure 1:
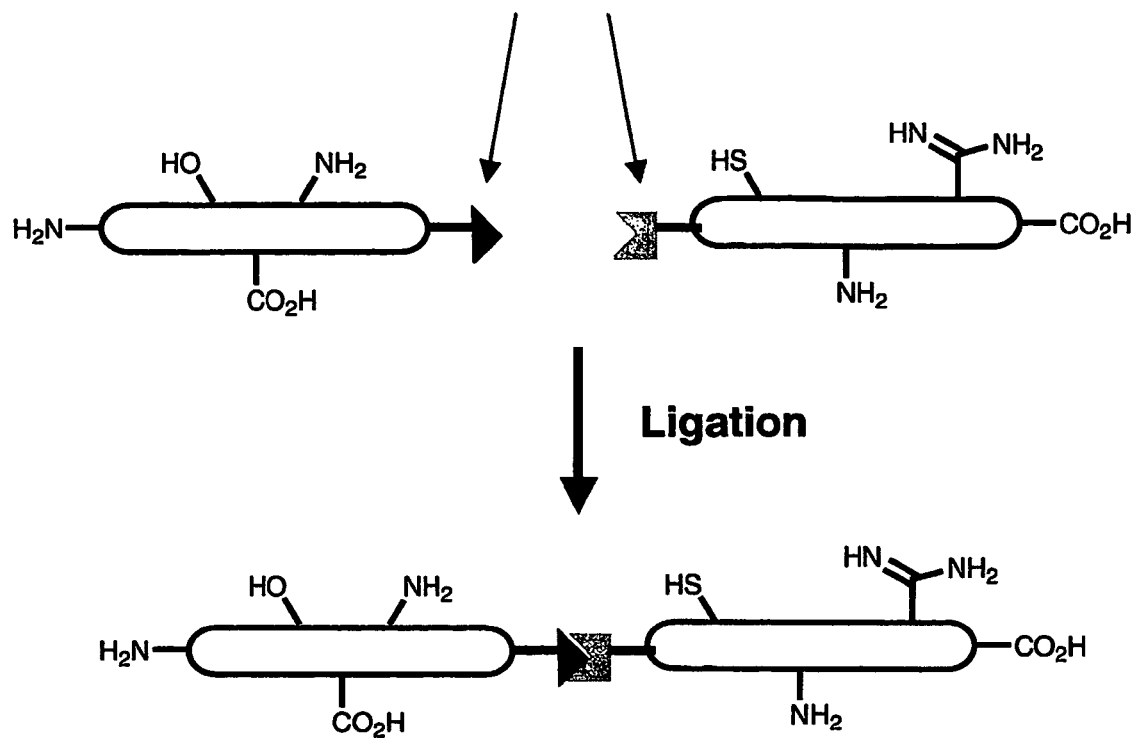
FIG. 1 illustrates schematically the general principle of chemical ligation.
Figure 2:
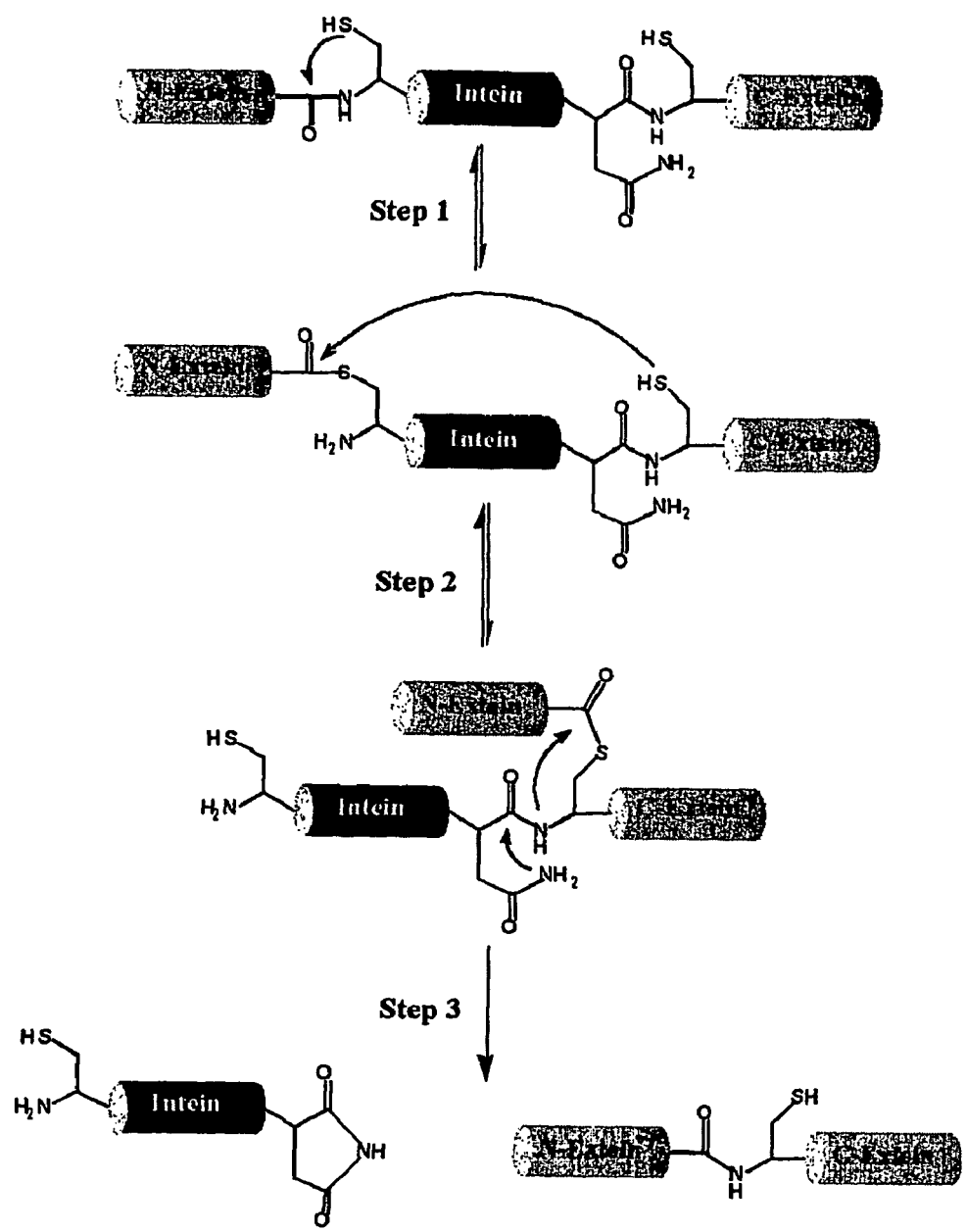
FIG. 2 illustrates schematically the mechanism of protein splicing.
Figure 3:
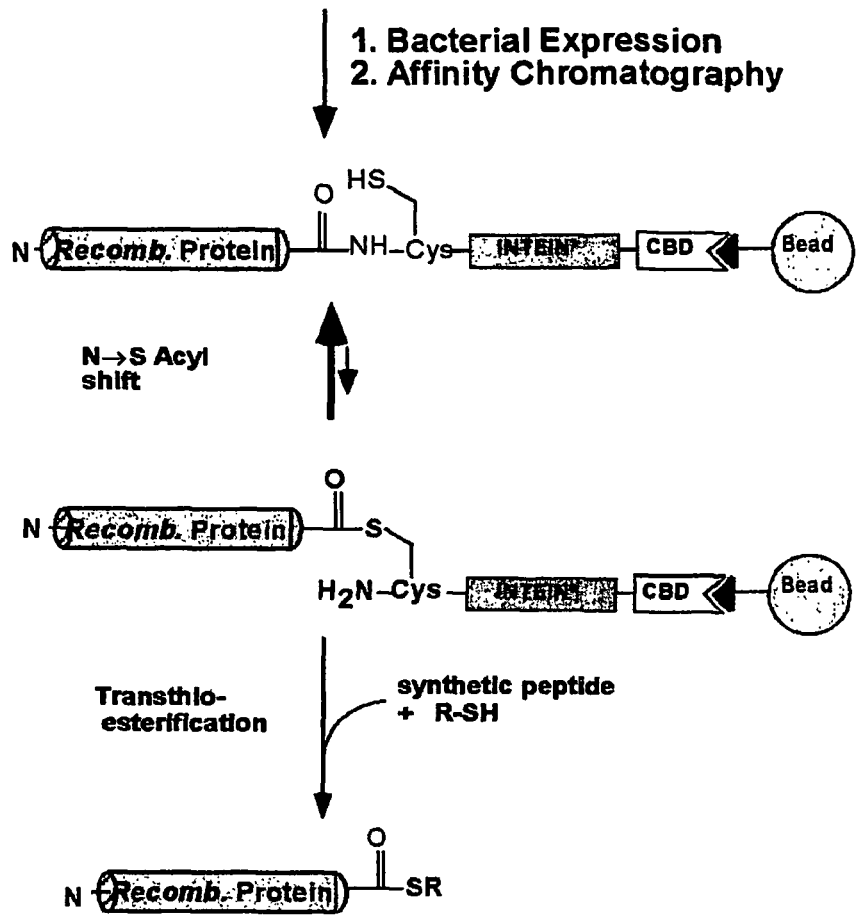
FIG. 3 illustrates the generation of recombinant C-terminal thioester proteins.
Figure 4:
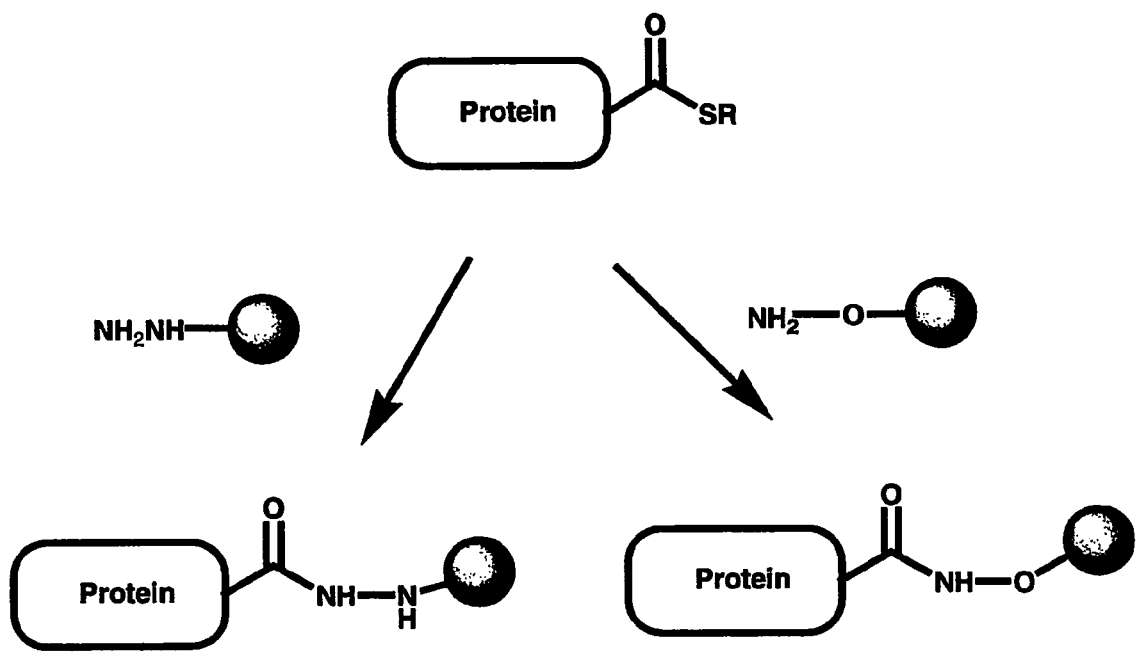
FIG. 4 illustrates ligation of protein and peptide thioesters with hydrazine and aminooxy containing entities, such as labels, peptides and proteins.
Figure 5:
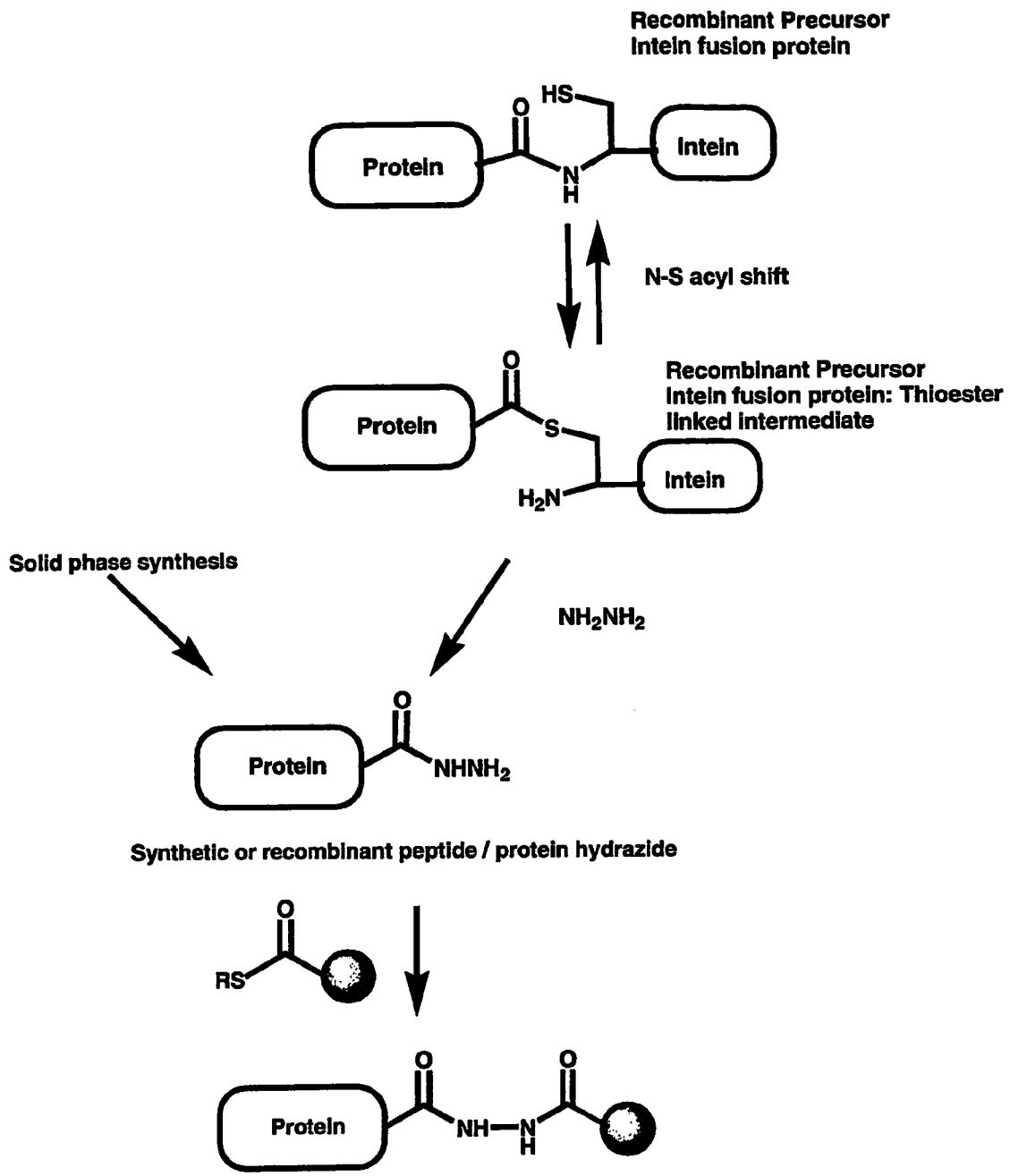
FIG. 5 illustrates the generation of synthetic and recombinant peptide hydrazides for ligation with thioester containing molecules. Note the peptide or label is is the acyl substituent of the thioester.
Figure 6:
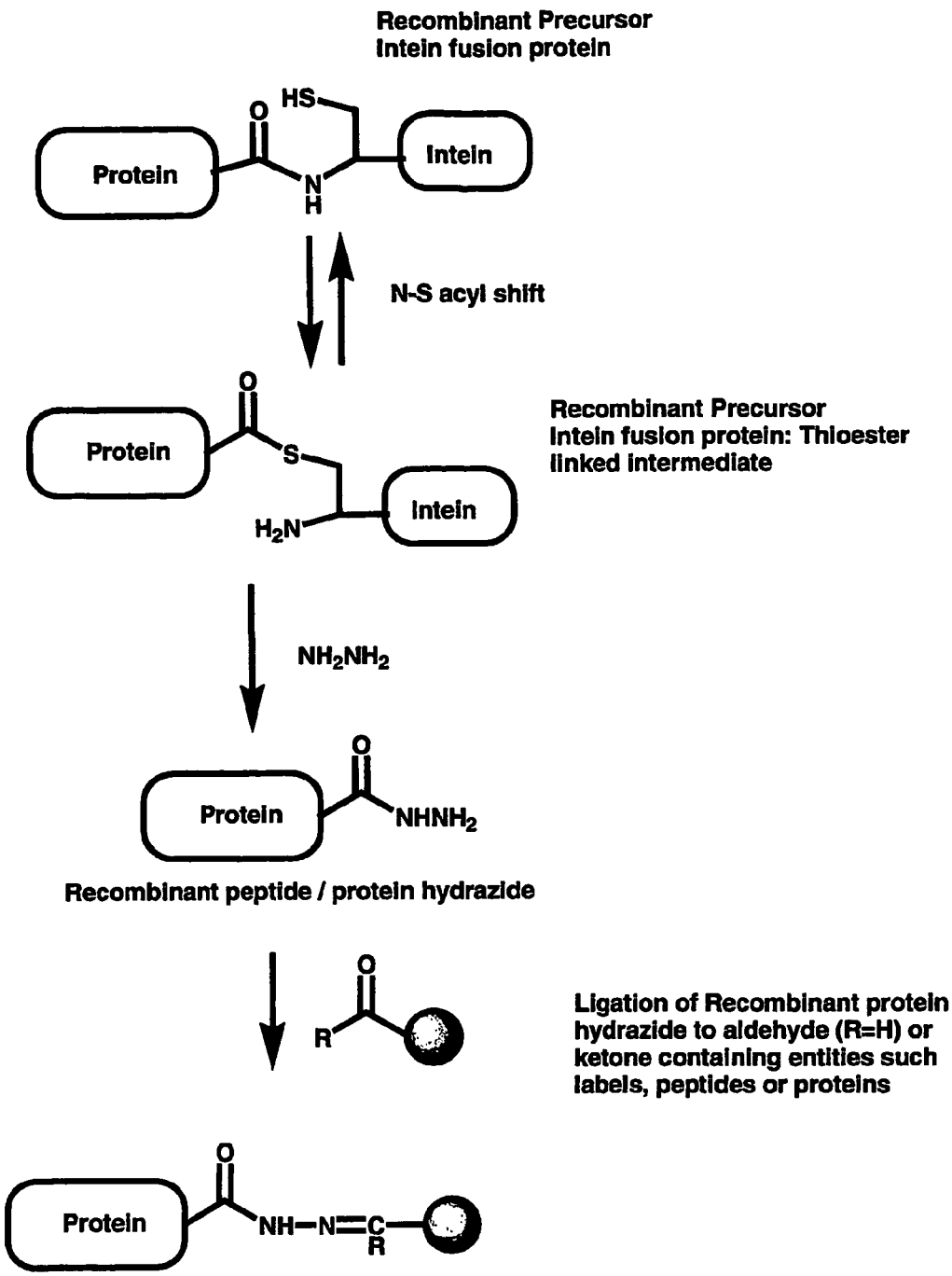
FIG. 6 illustrates the generation of recombinant peptide hydrazides for ligation with aldehyde and ketone containing molecules.
Figure 7:
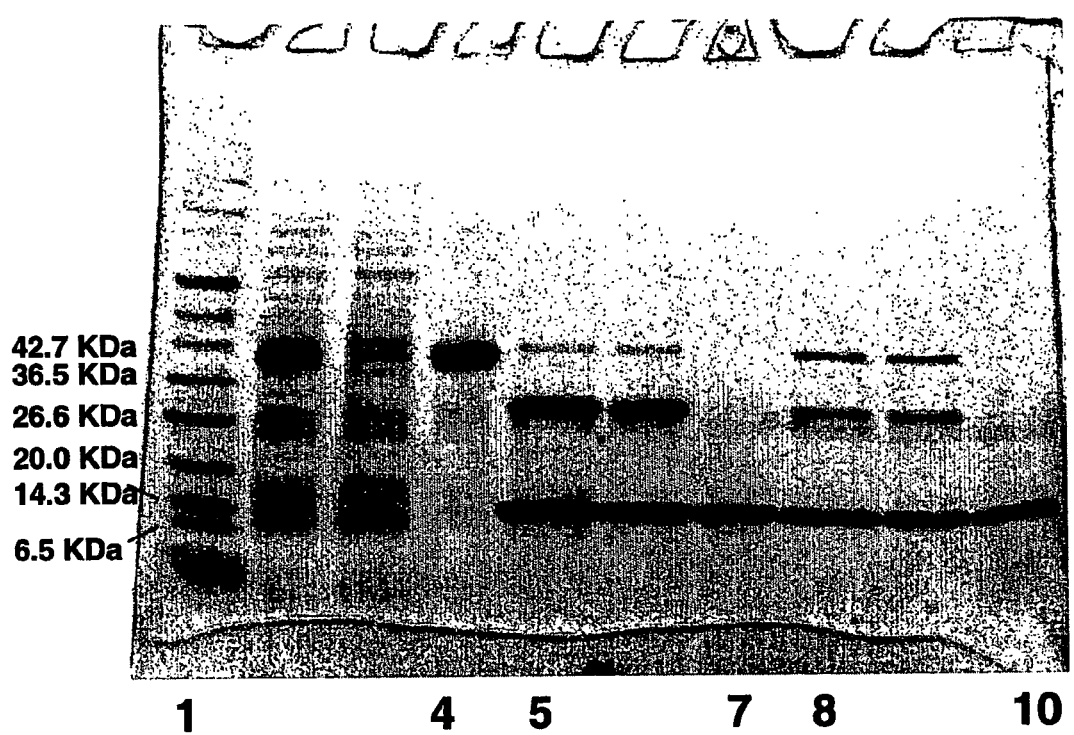

FIG. 7 illustrates SDS-PAGE analysis of Grb2-SH2-GyrA-CBD (immobilised on chitin beads) treated with DTT and MESNA. Molecular weight markers (lane 1); purified Grb2-SH2-GyrA-CBD immobilised on chitin beads (lane 4). Grb2-SH2-GyrA-CBD treated with 100 mM DTT (lanes 5 and 7) or 120 mM MESNA (lanes 8 and 10). Both the whole reaction slurries (lanes 5 and 8) and the reaction supernatants (lanes 7 and 10) were analysed.

Figure 8:
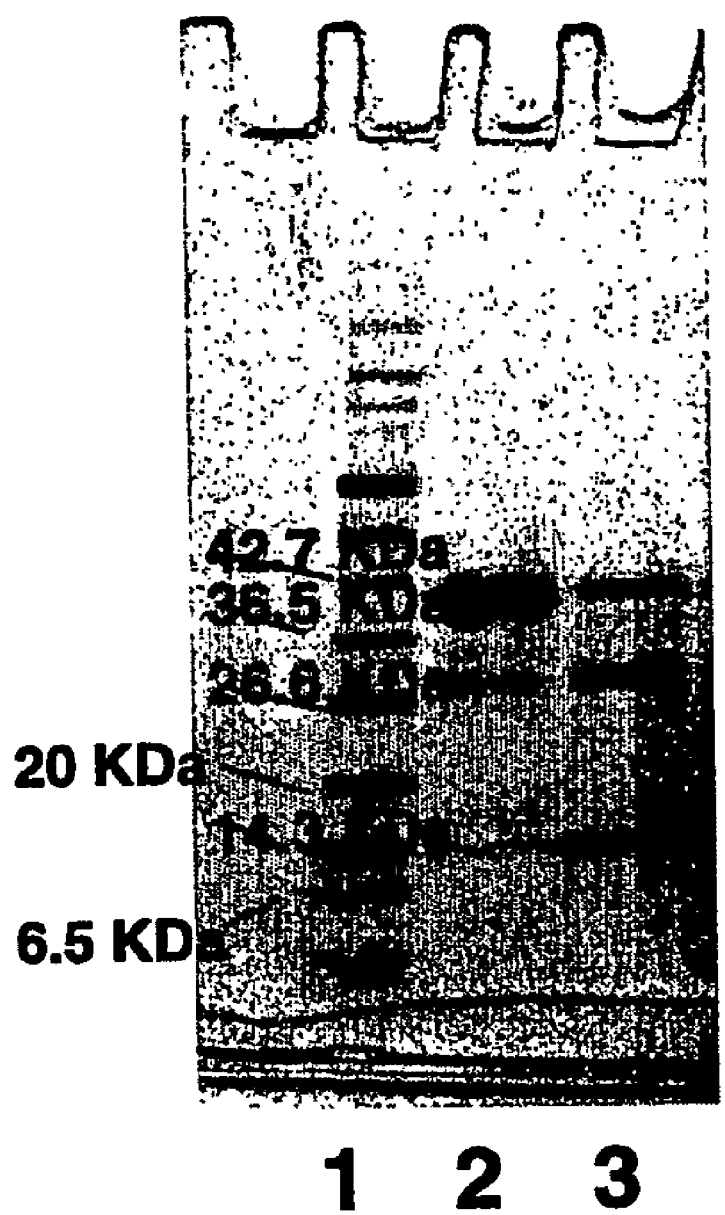

FIG. 8 illustrates SDS-PAGE analysis of Grb2-SH2-GyrA-CBD (immobilised on chitin beads) treated with hydrazine. Molecular weight markers (lane 1);

Purified Grb2-SH2-GyrA-CBD immobilised on chitin beads after 20 h treatment with phosphate buffer only (lane 2). Grb2-SH2-GyrA-CBD treated with 200 mM hydrazine in phosphate buffer for 20 h. The whole reaction slurries were analysed.

Figure 9:
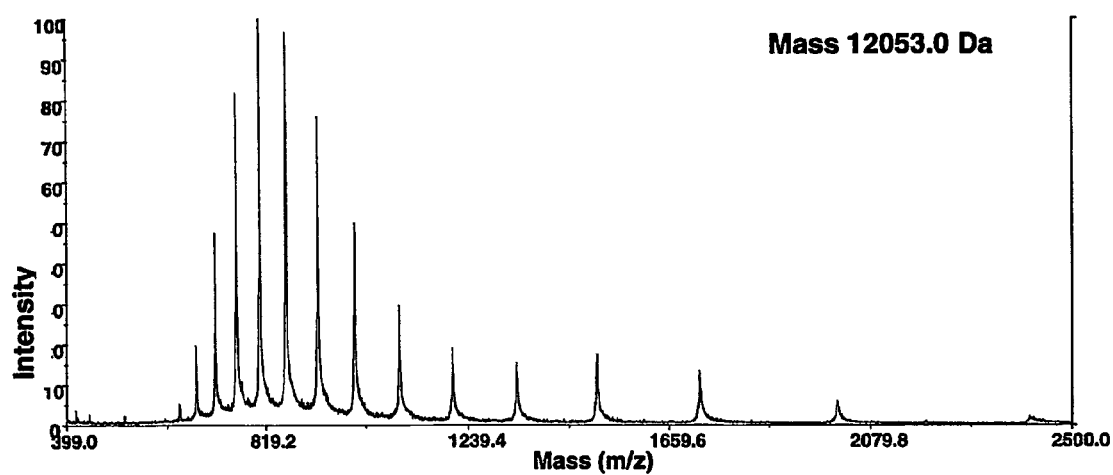

FIG. 9 illustrates an ESMS spectrum of the C-terminal hydrazide derivative of Grb2-SH2.

Figure 10:
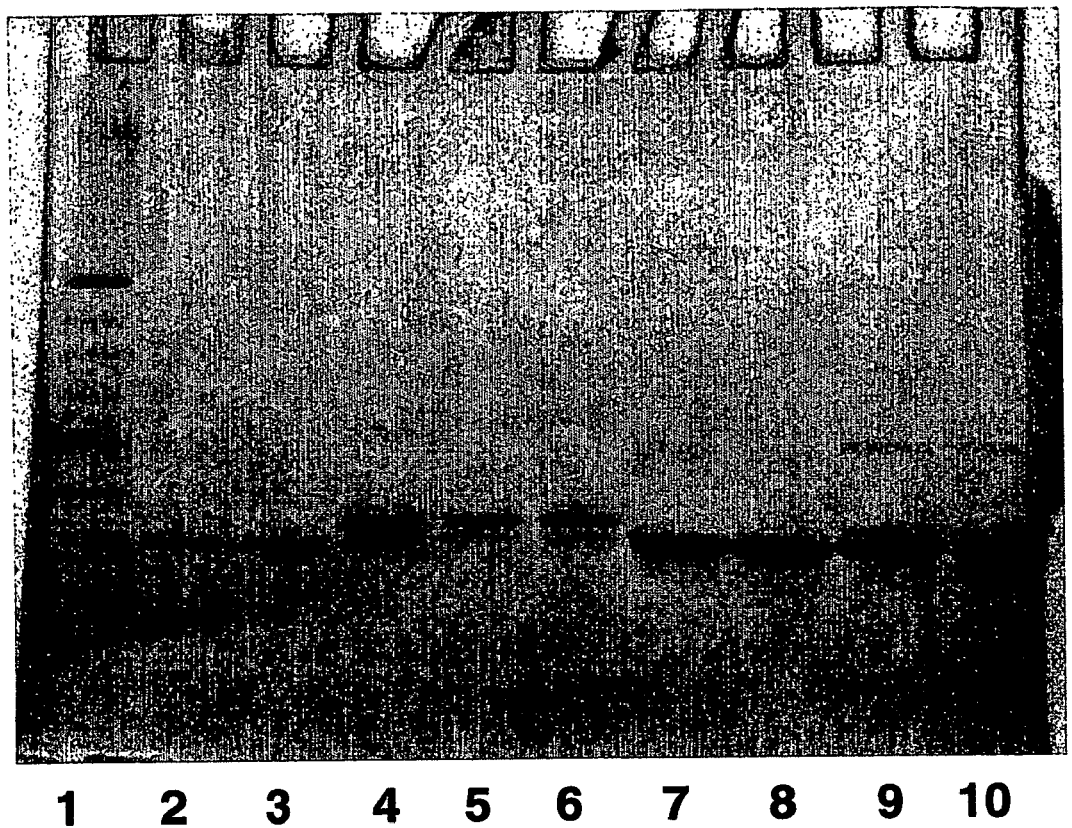

FIG. 10 shows SDS-PAGE analysis of the reaction between synthetic ketone containing peptide $CH_3COCO$-myc with Grb2-SH2-C-terminal hydrazide and Cytochrome C. Molecular weight markers (lane 1); Grb2-SH2-C-terminal DTT thioester (lane 2). Reaction between Grb2-SH2-C-terminal hydrazide and $CH_3COCO$-myc at time points t=0 h (lane 3), t=24 h (lane 4), t=48 h (lane 5) and t=72 h (lanes 6). Reaction between Cytochrome C and $CH_3COCO$-myc at time points t=0 h (lane 7), t=24 h (lane 8), t=48 h (lane 9) and t=72 h (lanes 10)

Figure 11:
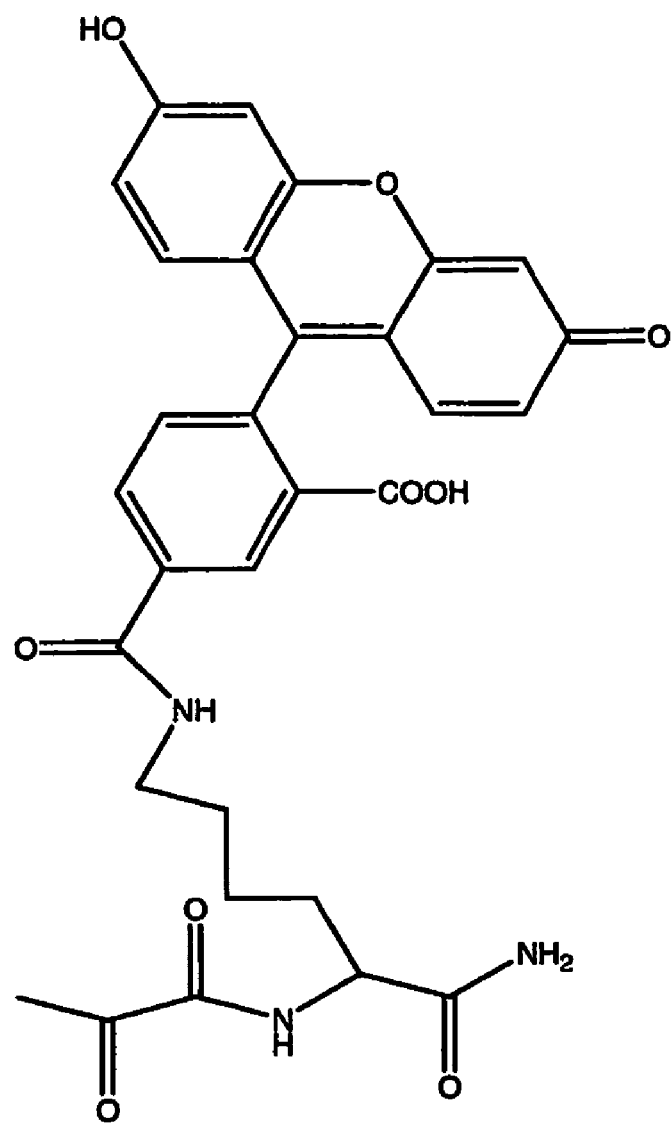

FIG. 11 shows the structure of $CH_3COCO$-Lys(F1). The 5-carboxy fluorescein positional isomer is shown.

Figure 12:
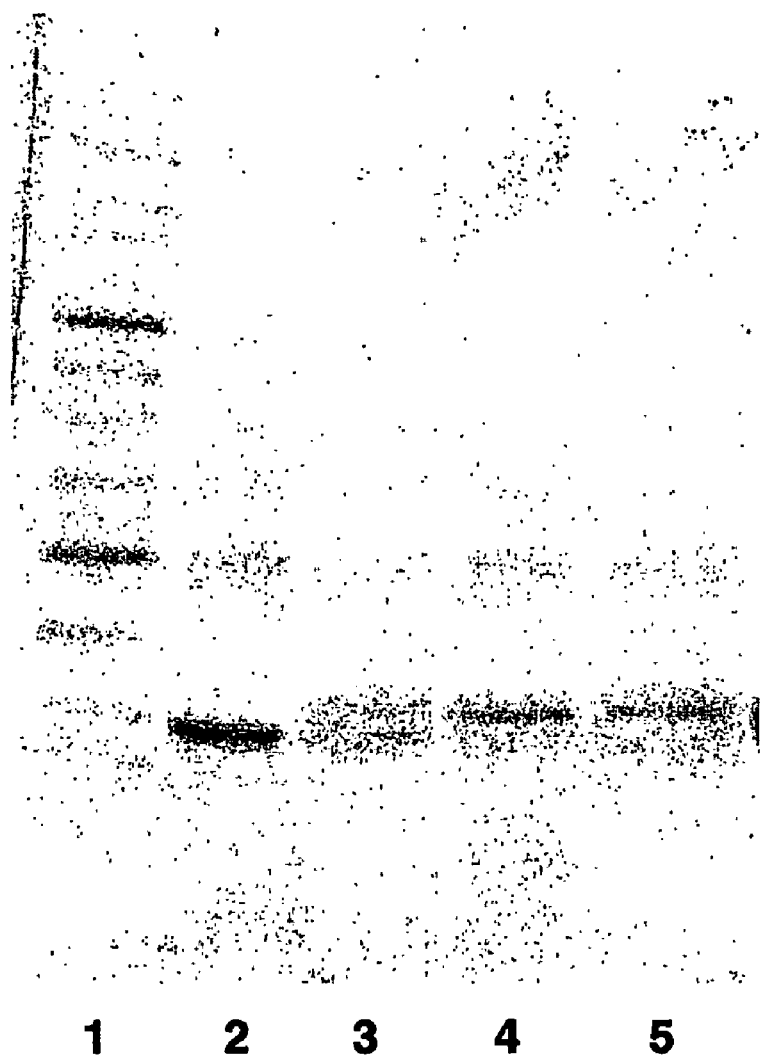

FIG. 12 illustrates SDS-PAGE analysis of the reaction between $CH_3COCO$-Lys(F1) with Grb2-SH2 C-terminal hydrazide in 50 mM sodium acetate buffer pH 4.5. Molecular weight markers (lane 1); Grb2-SH2 C-terminal hydrazide (lane 2). Reaction between Grb2-SH2 C-terminal hydrazide and $CH_3COCO$-Lys(F1) at time points t=4 h (lane 3), t=24 h (lane 4), t=48 h (lane 5)

Figure 13:
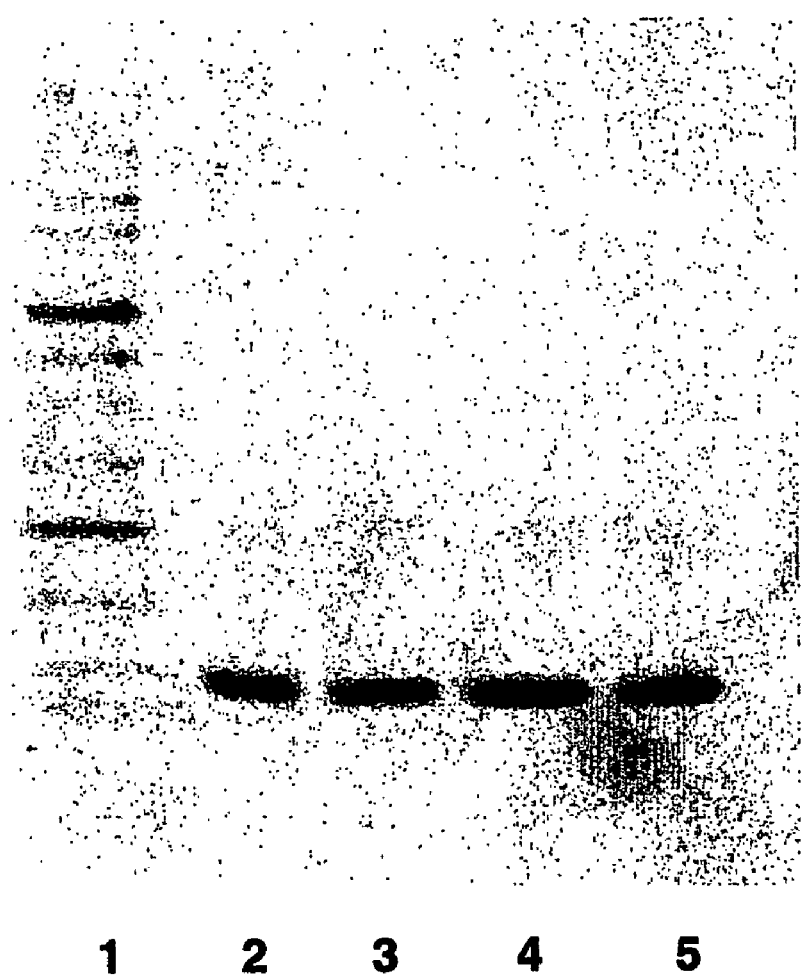

FIG. 13 illustrates SDS-PAGE analysis of the reaction between $CH_3COCO$-Lys(F1) with Cytochrome C in 100 mM sodium acetate buffer pH 4.5. Molecular weight markers (lane 1); Cytochrome C (lane 2). Reaction between Cytochrome C and $CH_3COCO$-Lys(F1) at time points t=4 h (lane 3), t=24 h (lane 4), t=48 h (lane 5).

Figure 14:
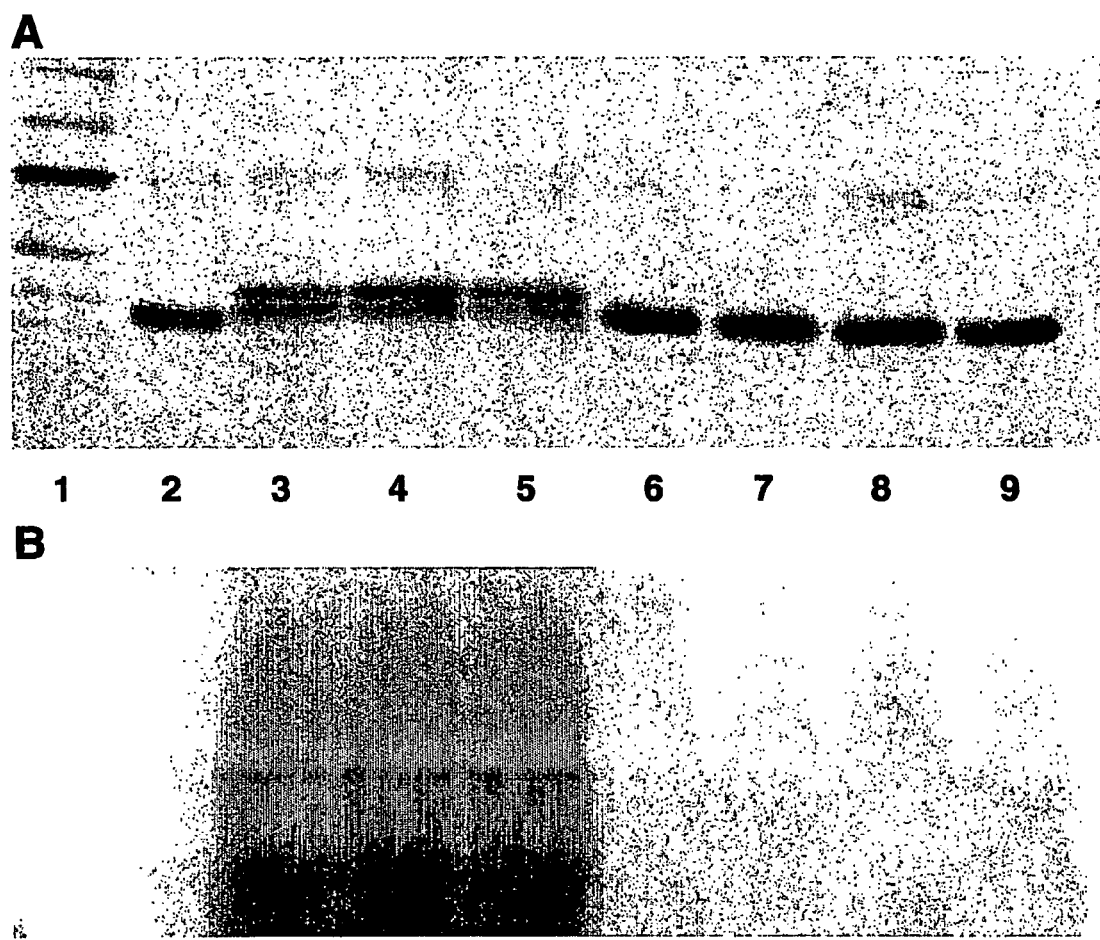

FIG. 14 illustrates SDS-PAGE analysis of the reaction of $CH_3COCO$-Lys(F1) with Grb2-SH2 C-terminal hydrazide and with Cytochrome C in 50 mM sodium acetate buffer pH 4.5.(A) total protein stain of gel. Prior to this coomassie staining (A), the gel was imaged for green fluorescence (B). Molecular weight markers (lane 1); Grb2 SH2 C-terminal hydrazide (lane 2); Reaction between Grb2 SH2 C-terminal hydrazide and $CH_3COCO$-Lys(F1) at time points t=4 h (lane 3), t=24 h (lane 4), t=48 h (lane 5). Cytochrome C (lane 6); Reaction between Cytochrome C and $CH_3COCO$-Lys(F1) at time points t=4 h (lane 7), t=24 h (lane 8) and t=48 h (lanes 9).

Figure 15:
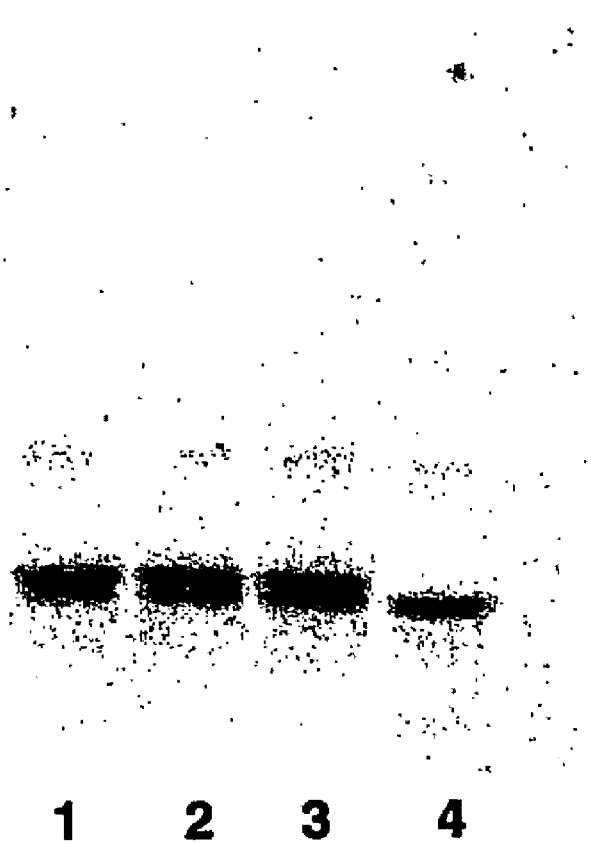

FIG. 15 shows SDS-PAGE analysis of the reaction between $CH_3COCO$-Lys(F1) and Grb2 SH2 C-terminal hydrazide in 40% aqueous acetonitrile containing 0.1% TFA; reaction after 4 h (lane 1), 24 h (lane 2), 48 h (lane 3), Grb2 SH2 C-terminal hydrazide (lane 4).

EXAMPLES

Example 1

Protein Ligation/Site Specific Protein Labelling Using the Reaction of Peptide/Protein Thioesters with Compounds Containing Hydrazine/Hydrazide or Aminoxy Functionalities A) Reaction of a Peptide C-Terminal Thioester with 100 mM Hydrazine at pH 6.0

200 mM sodium phosphate buffer pH 6.0 containing 100 mM hydrazine monohydrate (200 µL) was added to a model synthetic C-terminal thioester peptide termed AS626p1A (200 µg) to yield a final peptide concentration of 317 µM. AS626p1A has sequence ARTKQ TARK(Me)$_3$ STG-GKAPRKQ LATKAARK-COS-$(CH_2)_2$—$COOC_2H_5$ (SEQ ID NO: 1) wherein a single Alanine residue (which may be any one of the Alanine residues of SEQ ID NO: 1) is substituted by an Arginine residue. The reaction was incubated at room temperature and monitored with time by analytical reversed phase HPLC. Vydac C18 column (5 µM, 0.46×25 cm). Linear gradients of acetonitrile water/0.1% TFA were used to elute the peptides at a flow rate of 1 mL min$^{-1}$. Individual peptides eluting from the column were characterised by electrospray mass spectrometry.

B) Reaction of a Peptide C-Terminal Thioester with 100 mM Hydroxylamine at pH 6.0

200 mM sodium phosphate buffer pH 6.0 containing 100 mM hydroxylamine hydrogen chloride (200 µL) was added to AS626p1A (200 µg) to yield a final peptide concentration of 317 µM. The reaction was incubated at room temperature and monitored with time by analytical reversed phase HPLC. Vydac C18 column (5 µM, 0.46×25 cm). Linear gradients of acetonitrile water/0.1% TFA were used to elute the peptides at a flow rate of 1 mL min$^{-1}$. Individual peptides eluting from the column were characterised by electrospray mass spectrometry.

C) Reaction of a Peptide C-Terminal Thioester with 100 mM Hydroxylamine at pH 6.8

200 mM sodium phosphate buffer pH 6.8 containing 100 mM hydroxylamine hydrogen chloride (200 µL) was added to AS626p1A (200 µg) to yield a final peptide concentration of 317 µM. The reaction was incubated at room temperature and monitored with time by analytical reversed phase HPLC. Vydac C18 column (5 µM, 0.46×25 cm). Linear gradients of acetonitrile water/0.1% TFA were used to elute the peptides at a flow rate of 1 mL min$^{-1}$. Individual peptides eluting from the column were characterised by electrospray mass spectrometry.

D) Reaction of a Peptide C-Terminal Thioester with 10 mM Hydroxylamine at pH 6.8

The procedure as described in C) was repeated, replacing 100 mM hydroxylamine with 10 mM hydroxylamine.

E) Reaction of a Peptide C-Terminal Thioester with 10 mM Hydroxylamine at pH 7.5

The procedure as described in D) was repeated, at pH7.5.

F) Reaction of a Peptide C-Terminal Thioester with 2 mM Hydroxylamine at pH 7.5

The procedure as described in E) was repeated, replacing 10 mM hydroxylamine with 2 mM hydroxylamine.

G) Reaction of a Peptide C-Terminal Thioester with 100 mM O-Methylhydroxylamine ($NH_2$—O—$CH_3$) at pH 7.5

200 mM sodium phosphate buffer pH 7.5 containing 100 mM O-methylhydroxylamine (200 µL) was added to synthetic C-terminal thioester peptide AS626p1A (200 µg) to yield a final peptide concentration of 317 µM. The reaction was incubated at room temperature and monitored with time by analytical reversed phase HPLC. Vydac C18 column (5 µM, 0.46×25 cm). Linear gradients of acetonitrile water/0.1% TFA were used to elute the peptides at a flow rate of 1 mL $min^{-1}$. Individual peptides eluting from the column were characterised by electrospray mass spectrometry.

H) Reaction of a Peptide C-Terminal Thioester with 10 mM O-Methylhydroxylamine at pH 7.5

The procedure as described in G) was repeated, replacing 100 mM O-methylhydroxylamine with 10 mM O-methylhydroxylamine.

I) Reaction of a Recombinant Protein C-Terminal Thioester with 100 mM O-Methylhydroxylamine at pH 7.5

The C-terminal mercaptoethanesulfonic acid thioester derivative of recombinant Grb2-SH2, was generated through cleavage of the fusion protein Grb2-SH2-GyrA intein-CBD as described in Example 2 below. This recombinant C-terminal thioester protein (100 µg) was reacted with 100 mM O-methylhydroxylamine in 200 mM sodium phosphate buffer pH 7.5 (200 µL). The reaction was incubated at room temperature and monitored with time by analytical reversed phase HPLC. Vydac C5 column (5 µM, 0.46×25 cm). Linear gradients of acetonitrile water/0.1% TFA were used to elute the peptides at a flow rate of 1 mL $min^{-1}$. Individual peptides eluting from the column were characterised by electrospray mass-spectrometry.

Results

These examples demonstrate the novel strategy for protein ligation/site specific protein labelling of both synthetic and recombinant protein sequences of the invention using the reaction of peptide/protein C-terminal thioesters with compounds containing hydrazine/hydrazide or aminoxy functionalities.

As described above, a purified synthetic 27 amino acid C-terminal thioester peptide (the ethyl 3-mercaptopropionate thioester derivative) was treated with hydrazine and hydroxylamine under various conditions (Table 1).

Treatment with 100 mM hydrazine at pH 6.0 formed a peptide species that eluted earlier than the starting thioester peptide as analysed by HPLC. This material was identified as the expected peptide hydrazide by ESMS: observed mass=3054 Da, expected (av. isotope comp) 3053 Da. The reaction of the peptide C-terminal thioester with hydrazine to form the peptide hydrazide was monitored with time by reverse phase HPLC. Only the desired material was formed with no side product formation even after 3 days. The stability of the peptide hydrazide, under the reaction conditions, indicates that the reaction occurs at the C-terminal thioester moiety and is chemoselective in nature. It also highlights the applicability of this reaction for protein ligation and labelling (2 h 70% conversion , 4 h>95% conversion).

To ascertain whether aminooxy containing compounds chemoselectively react with peptide/protein C-terminal thioesters, to afford protein ligation and site-specific labelling, a synthetic C-terminal thioester peptide was treated with hydroxylamine under various conditions (Table 1).

A purified synthetic 27 amino acid C-terminal thioester peptide (ethyl 3-mercaptopropionate thioester, observed mass 3155 Da) was incubated at room temperature with different hydroxylamine concentrations in aqueous buffers of varying pH. In all cases the peptide C-terminal thioester reacted to form a single product that eluted earlier than the starting thioester peptide as analysed by reverse phase HPLC. This material corresponds to the expected hydroxamic acid peptide as determined by ESMS: observed mass=3052 Da, expected (av. isotope comp) 3054 Da. The kinetics of the reaction were monitored using reverse phase HPLC. The peptide C-terminal thioester was converted to the corresponding peptide hydroxamic acid in a clean fashion with no side-product formation. Increasing the pH of the reaction buffer accelerated the rate of reaction. For instance, with a concentration of 100 mM $NH_2OH$, on moving from pH 6.0 to pH 6.8 the percentage product formation after 1 h increased from 25% to 91%. The rate of reaction with 100 mM $NH_2OH$ at pH 6.0, was comparable with 10 mM $NH_2OH$ at pH 6.8.

The rate of reaction of the peptide C-terminal thioester with hydroxalymine, to form the corresponding hydroxamic acid, increases with increasing pH and decreases with decreasing $NH_2OH$ concentrations. To identify conditions of pH and reactant concentration suitable for peptide/protein labelling and ligation, the labelling was performed under increasing pH and decreasing $NH_2OH$ concentrations.

The reaction with 10 mM $NH_2OH$ was 83% complete after 4 h at pH 6.8, while at pH 7.5 it was 83% complete after 2 h. On further decreasing the $NH_2OH$ concentration to 2 mM the reaction rate at pH 7.5 decreased markedly, 70% of the starting peptide α-thioester being converted to the corresponding hydroxamic acid after 8 hrs. It was noted that a small amount of a side-product, corresponding in mass to the peptide acid, was formed during the reaction. Presumably this was formed by a competing hydrolysis side reaction at pH 7.5, which was not observed with 10 mM $NH_2OH$ at pH 7.5 due to the faster reaction at this higher reactant concentration.

TABLE 1

| | | | Percentage product formation with time | | | | |
|---|---|---|---|---|---|---|---|
| Reactant | Concentration | pH | 1 hr | 2 hr | 4 hr | 8 hr | 72 hr |
| $NH_2NH_2$ | 100 mM | 6.0 | — | 70 | 100 | | |
| $NH_2OH$ | 100 mM | 6.0 | 25 | 48.1 | 76.3 | — | 100 |
| $NH_2OH$ | 100 mM | 6.8 | 91 | 100 | | | |
| $NH_2OH$ | 10 mM | 6.8 | 26 | — | 83 | 100 | |
| $NH_2OH$ | 10 mM | 7.5 | — | 82.7 | 100 | 100 | |
| $NH_2OH$ | 2 mM | 7.5 | 11.2 | 17 | 38 | 70 | 80* |

*All starting material has reacted with 80% conversion to the desired product and ~20% to the hydrolysis side-product.

To further investigate the chemoselective reaction of aminooxy containing compounds with peptide/protein C-terminal thioesters, to afford protein ligation and site-specific labelling, the synthetic C-terminal thioester peptide AS626p1 was treated with O-methylhydroxylamine.

The purified synthetic 27 amino acid C-terminal thioester peptide (ethyl 3-mercaptopropionate thioester, observed mass 3155 Da) was incubated at room temperature with 100 mM D-methylhydroxylamine in 200 mM sodium phosphate buffer pH 7.5. The peptide C-terminal thioester reacted to form a single product that eluted earlier than the starting thioester peptide as analysed by reverse phase HPLC. This material corresponded to the expected N-methoxy peptide amide as determined by ESMS: observed mass 3070 Da, expected mass 3068 Da. The kinetics of the reaction were monitored using reverse phase HPLC (Table II). The peptide C-terminal thioester was converted to the corresponding N-methoxy peptide amide derivative in a clean fashion with no side-product formation, with the reaction 75% complete after 24 h. Under these conditions no thioester hydrolysis was observed.

TABLE II

| Reactant | Concentration | pH | \multicolumn{5}{c|}{Percentage product formation with time} |
|---|---|---|---|---|---|---|---|
| | | | 1 hr | 2 hr | 5 hr | 24 hr | 72 hr |
| NH$_2$OCH$_3$ | 100 mM | 7.5 | — | | 7.5 | 28 | 76 |

When the reaction was repeated under the same conditions but with 10 mM O-methylhydroxylamine replacing 100 mM O-methylhydroxylamine, the reaction rate was slower. However, after 72 h, 88% of the starting C-terminal thioester peptide had reacted. Under these conditions side-product formation was observed, in addition to the desired reaction product formation. Even so, after 72 h, 30-40% of the reaction product was estimated to be the desired ligation reaction product (N-methoxy peptide amide) from HPLC analysis of the reaction mixture.

The reaction of O-methylhydroxylamine with recombinant C-terminal thioester proteins was also investigated. Recombinant Grb2-SH2 was generated as the C-terminal mercaptoethanesulfonic acid thioester derivative, through thiol mediated cleavage of the fusion protein Grb2-SH2-GyrA intein-CBD, as described in Example 2. This recombinant C-terminal thioester protein was reacted with 100 mM O-methylhydroxylamine at pH 7.5. Analysis of the reaction mixture after 18 h by HPLC and ESMS showed that all of the C-terminal thioester protein had been completely converted into two protein species. These two protein derivatives corresponded to the desired ligation reaction product, namely Grb2-SH2 C-terminal N-methoxy amide (expected mass 12067 Da; observed mass 12067 Da), and an oxidised form of the desired reaction product (observed mass 12084 Da). No side products corresponding to hydrolysis of the C-terminal protein thioester were observed. Thus all of the C-terminal thioester recombinant protein had chemoselectively ligated with O-hydroxylamine, via an amide bond forming reaction specifically at the C-terminus of the protein. i.e. the reaction afforded site-specific C-terminal labelling of the recombinant protein.

Example 2

Generation of Recombinant C-Terminal Hydrazide Grb2 SH2 Protein

To investigate (i) the ability to generate recombinant C-terminal hydrazide proteins through the selective cleavage of protein-intein fusions with hydrazine, and (ii) their subsequent use in ligation/labelling reactions, the SH2 domain of the adapter protein Grb2 was chosen as a model system.

Sequence of human Grb2 SH2 domain
HPW FFGKIPRAKA EEMLSKQRHD GAFLIRESES APGDFSLSVK FGNDVQHFKV LRDGAGKYFL WVVK-FNSLNE LVDYHRSTSV SRNQQIFLRD IEQVPQQPT (SEQ ID NO:2)

Expression of Grb2-SH2 Domain-GyrA Intein Fusion

The DNA sequence encoding the SH2 domain of human Grb2 appended at its C-terminus with an extra glycine residue was cloned into the pTXB1 expression plasmid (NEB). This vector pTXB1$_{Grb2-SH2\ (Gly)}$ encodes for a fusion protein whereby the SH2 domain of Grb2 is linked via a glycine residue to the N-terminus of the GyrA intein, which is in turn fused to the N-terminus of a chitin binding domain region (CBD). E. coli cells were transformed with this plasmid and grown in LB medium to mid log phase and protein expression induced for 4 h at 37° C. with 0.5 mM IPTG. After centrifugation the cells were re-suspended in lysis buffer (0.1 mM EDTA, 250 mM NaCl, 5% glycerol, 1 mM PMSF, 25 mM HEPES, pH 7.4) and lysed by sonication. The soluble fraction was loaded onto a chitin column pre-equilibrated in lysis buffer. The column was then washed with wash buffer (1 mM EDTA, 250 mM NaCl, 0.1% Triton-X 100, 25 mM HEPES, pH 7.0) to yield purified Grb2-SH2-GyrA-CBD immobilised on chitin beads (FIG. 7).

Generation of Grb2-SH2 C-Terminal Thioesters by Thiol Induced Cleavage of the Grb2-SH2-GyrA Intein Fusion To ascertain that the intein domain within the protein was functional the fusion protein was exposed to thiols to assess the extent of cleavage via transthioesterification. Chitin beads containing immobilised Grb2-SH2-GyrA-CBD were equilibrated into 200 mM NaCl, 200 mM phosphate buffer pH 7.4. Dithiothreitol (DTT) or 2-mercaptoethanesulfonic acid (MESNA) were then added to the beads in 200 mM NaCl, 200 mM phosphate buffer pH 7.4 to give a 50% slurry with a final thiol concentration of 100 mM or 120 mM respectively. The mixtures were then rocked at room temperature and aliquots analysed by SDS-PAGE. After 48 hours the supernatants from the reactions were isolated and subsequently analysed by HPLC and ESMS.

Treatment of Grb2-SH2-GyrA intein-CBD fusion with both DTT and MESNA resulted in cleavage of the fusion protein into two protein species (FIG. 7). The molecular size of the two fragments corresponds to that of the Grb2-SH2 and the GyrA-intein fusion, indicative that cleavage has taken place at the SH2-intein junction. Cleavage of the precursor fusion protein liberated the SH2 domain into the supernatant while the GyrA intein-CBD portion remained immobilized on the chitin beads. After cleavage with both DTT or MESNA, ESMS analysis of the supernatants confirmed that the Grb2-SH2 was generated as either the expected DTT or MESNA C-terminal thioester derivatives respectively.

Expected mass of Grb2-SH2 DTT-C-terminal thioester=12173.9 Da; observed mass 12173.5 Da. Expected mass of Grb2-SH2 MESNA-C-terminal thioester=12162.0 Da; observed mass 12163.0 Da.

Generation of Grb2-SH2 C-terminal Hydrazide by Hydrazine Induced Cleavage of the Grb2-SH2-GyrA Intein Fusion.

The inventors hypothesised that the thioester linkage between Grb2-SH2 and the GyrA intein in the precursor fusion protein is cleaved with hydrazine. The chemoselective reaction of hydrazine, at the thioester moiety linking Grb2 SH2 to the intein, would liberate the Grb2-SH2 domain into the supernatant as its corresponding C-terminal hydrazide derivative. Chitin beads containing immobilised Grb2-SH2-GyrA-CBD were therefore equilibrated into 200 mM NaCl, 200 mM phosphate buffer pH 7.4 and hydrazine monohydrate added in the same buffer to give a 50% slurry with a final hydrazine concentration of 200 mM. The mixture was then rocked at room temperature and analysed by SDS-PAGE (FIG. 8). After 20 hours the supernatant was removed and analysed by HPLC and ESMS.

Treatment of Grb2-SH2-GyrA intein-CBD fusion with hydrazine resulted in cleavage of the fusion protein into two species. The molecular size of the two fragments as analysed by SDS-PAGE corresponded to Grb2-SH2 and the GyrA-intein fusion, indicative that cleavage has taken place at the unique thioester linkage between the SH2 and intein domains. Cleavage of the precursor fusion protein liberated the SH2 domain into the supernatant while the GyrA intein-CBD portion remained immobilized on the chitin beads. HPLC and ESMS analysis of the cleavage supernatant confirmed that a single protein species was generated that corresponds to the C-terminal hydrazide derivative of Grb2-SH2. Expected mass of Grb2-SH2 C-terminal hydrazide=12051.7 Da; observed mass 12053.0 Da. (FIG. 9)

After 20 h of reaction Grb2-SH2 C-terminal hydrazide was isolated from the supernatant by either (i) using RPHPLC followed by lyophilisation or (ii) by gel filtration. In this later approach the Grb2-SH2 C-terminal hydrazide reaction solution was loaded onto a superdex peptide column (Amersham Biosciences) and eluted with a running buffer of 50 mM sodium acetate pH 4.5. This yielded a solution of purified Grb2-SH2 C-terminal hydrazide in 50 mM sodium acetate pH 4.5. This solution was concentrated using a centricon filter (3000 MWCO), then snap frozen and stored at −20° C. until use.

A sample of the purified and lyophilised Grb2-SH2 C-terminal hydrazide (100 μg) was treated with the protease Lys-C (5 μg) in 100mM ammonium bicarbonate buffer pH 8.2 (100 μL). After incubating at 30° C. overnight the reaction was lyophilised and analysed by MALDI mass spectrometry. The observed mass of the C-terminal proteolytic fragment (FNSLNELVDYHRSTSVSRNQQIFLRDIEQVPQQPTG) (SEQ ID NO:3) (corresponds to that of the desired C-terminal hydrazide derivative (expected mass of C-terminal hydrazide proteolytic fragment 4229 Da; observed mass 4231 Da).

Example 3

Generation of Recombinant C-Terminal Hydrazide Maltose Binding Protein

As a further demonstration of the described approach, for generating recombinant C-terminal hydrazide proteins through the selective cleavage of protein-intein fusions with hydrazine, the generation of the C-terminal hydrazide derivative of maltose binding protein (MBP) was investigated.

```
Sequence of human MEP used
M K I E E G K L V I W I N G D K G Y N G L A E V G
K K F E K D T G I K V T V E H P D K L E E K F P Q
V A A T G D G P D I I F W A H D R F G G Y A Q S G
L L A E I T P D K A F Q D K L Y P F T W D A V R Y
N G K L I A Y P I A V E A L S L I Y N K D L L P N
P P K T W E E I P A L D K E L K A K G K S A L M F
N L Q E P Y F T W P L I A A D G G Y A F K Y E N G
K Y D I K D V G V D N A G A K A G L T F L V D L I
K N K H M N A D T D Y S I A E A A F N K G E T A M
T I N G P W A W S N I D T S K V N Y G V T V L P T
F K G Q P S K P F V G V L S A G I N A A S P N K E
L A K E F L E N Y L L T D E G L E A V N K D K P L
G A V A L K S Y E E E L A K D P R I A A T M E N A
Q K G E I M P N I P Q M S A F W Y A V R T A V I N
A A S G R Q T V D E A L K D A Q T N S S S N N N N
N N N N N N L G I E G R G T L E G (SEQ ID NO:4)
```

Expression of MBP-Sce VMA Intein Fusion.

The expression vector pMYB5 (New England Biolabs) encodes for a fusion protein comprising maltose binding protein (sequence above) fused N-terminal to the Sce VMA intein, which is in turn fused to the N-terminus of a chitin binding domain (CBD) to facilitate purification.

E. coli cells were transformed with this plasmid and grown in LB medium to mid log phase and protein expression induced for 4 h at 37° C. with 0.5 mM IPTG. After centrifugation the cells were re-suspended in lysis buffer (0.1 mM EDTA, 250 mM NaCl, 5% glycerol, 1 mM PMSF, 25 mM HEPES, pH 7.4) and lysed by sonication. The soluble fraction was loaded onto a chitin column pre-equilibrated in lysis buffer. The column was then washed with wash buffer (1 mM EDTA, 250 mM NaCl, 0.1% Triton-X 100, 25 mM HEPES, pH 7.0) to yield the purified fusion protein (MBP-VMA-CBD) immobilised on chitin beads.

Generation of MBP C-Terminal Thioesters by Thiol Induced Cleavage of the MBP-VMA-Intein Fusion Protein.

To ascertain that the intein domain within MBP-VMA-CBD was functional, the fusion protein was exposed to 2-mercaptoethanesulfonic acid (MESNA) to assess the extent of cleavage via transthioesterification. Chitin beads containing immobilised MBP-VMA-CBD were equilibrated into 200 mM NaCl, 200 mM phosphate buffer pH 7.4. MESNA was then added to the beads in 200 mM NaCl, 200 mM phosphate buffer pH 7.4 to give a 50% slurry with a final thiol concentration of 120 mM. The mixture was then rocked at room temperature and aliquots analysed by SDS-PAGE. After 48 hours the supernatants from the reactions were isolated and subsequently analysed by HPLC and ESMS.

Treatment of MBP-VMA-CBD fusion with MESNA results in cleavage of the fusion protein into two protein species. The molecular size of the two fragments corresponds to that of the MBP and the VMA-CBD portion, indicative that cleavage has taken place at the MBP-VMA intein junction. Cleavage of the precursor fusion protein liberates MBP into the supernatant while the VMA-CBD portion remains immobilized on the chitin beads. This was confirmed by ESMS analysis of the cleavage supernatant, which contained one protein species. Expected mass of MBP C-terminal MESNA thioester 43064 Da; observed mass 43098 Da.

Generation of MBP C-Terminal Hydrazide by Hydrazine Induced Cleavage of the MBP-VMA Intein Fusion Protein.

Chitin beads containing immobilised MBP-VMA-CBD were equilibrated into 200 mM NaCl, 200 mM phosphate buffer pH 7.4 and hydrazine monohydrate added in the same buffer to give a 50% slurry with a final hydrazine concentration of 200 mM. The mixture was then rocked at room temperature and analysed by SDS-PAGE and by HPLC and ESMS.

After 20 h of reaction MBP C-terminal hydrazide was isolated from the supernatant by either (i) using RPHPLC followed by lyophilisation or (ii) by gel filtration. In this later approach the MBP C-terminal hydrazide reaction solution was loaded onto a superdex peptide column (Amersham Biosciences) and eluted with a running buffer of 50 mM sodium acetate buffer pH 4.5. This yielded a solution of purified MBP C-terminal hydrazide in 50 mM sodium acetate buffer pH 4.5. This protein solution was concentrated using a centricon filter (3000 MWCO), then snap frozen and stored at −20° C. until use.

Treatment of MBP-VMA-CBD fusion with hydrazine results in cleavage of the fusion protein into two species. The molecular size of the two fragments as analysed by SDS-PAGE corresponds to MBP and the VMA-CBD portion, indicative that cleavage has taken place at the unique thioester linkage between the MBP-VMA intein domain. Cleavage of the precursor fusion protein liberates MBP into the supernatant, while the VMA-CBD portion remains immobilized on the chitin beads. HPLC and ESMS analysis of the cleavage supernatant confirms that a single protein species is generated with an observed mass of 42988 Da. The expected mass difference between the C-terminal MESNA thioester derivative of a protein and its corresponding C-terminal hydrazide is 111 Da. The observed mass of the C-terminal MESNA thioester of MBP was found to be 43098 Da. Thus the product from the hydrazine cleavage of MBP-VMA-CBD is 110 Da lower, indicating that the desired C-terminal hydrazide derivative of MBP had been formed.

Example 4

Ligation of Aldehyde and Ketone Containing Peptides and Labels to Recombinant C-Terminal Hydrazide Containing Proteins: Ligation of a Synthetic Peptide c-myc to Recombinant Grb2 SH2 Domain The inventors hypothesised that recombinant protein C-terminal hydrazides, generated by hydrazine treatment of the corresponding intein fusion precursor, can be site-specifically modified by chemoselective ligation with aldehyde and ketone containing peptides and labels. To demonstrate such an approach, the ability of a synthetic ketone containing peptide to ligate with the Grb2-SH2 C-terminal hydrazide generated above was investigated. A synthetic peptide corresponding to the c-myc epitope sequence was synthesised GEQKLISEEDL-NH$_2$ (SEQ ID NO:6), whereby pyruvic acid was coupled to the amino terminus of the peptide as the last step of the assembly. This peptide (designated CH$_3$COCO-myc) was purifed to >95% purity by RPHPLC and lyophilised (ESMS expected monoisotopic mass 1328.6 Da; observed mass 1328.6 Da).

A sample of CH$_3$COCO-myc peptide was dissolved in 100 mM sodium acetate buffer pH 4.5 to give a 4 mM peptide concentration. This peptide solution (100 μL) was then added to an aliquot of lyophilised Grb2-SH2 C-terminal hydrazide protein (~250 μg) and the reaction monitored by SDS-PAGE (FIG. 10) As a control CH$_3$COCO-myc was also incubated with Cytochrome C, a protein of similar same size to Grb2-SH2 but absent of a hydrazide functionality.

SDS-PAGE analysis shows that CH$_3$COCO-myc peptide has indeed ligated with Grb2-SH2 C-terminal hydrazide, as indicated by the conversion of Grb2-SH2 C-terminal hydrazide into a protein species of a higher molecular weight (approximately 1000-2000 Da higher). The reaction is virtually complete after 24 h and the reaction product appears to be stable. On the other hand, there was no observable change to Cytochrome C with time i.e no ligation, establishing that the ligation reaction is occurring at the C-terminal hydrazide functionality of Grb2-SH2.

After 96 h of reaction the product from the Grb2-SH2 ligation reaction was isolated by HPLC and characterised by ESMS. Chemoselective ligation of CH$_3$COCO-myc to Grb2-SH2 C-terminal hydrazide via hydrazone bond formation would give a product of expected mass 13363.7 Da. The observed product mass was 13364.1 Da indicting that the desired ligation product had been formed.

Example 5

Ligation of Aldehyde and Ketone Containing Peptides and Labels to Recombinant C-Terminal Hydrazide Containing Proteins: Fluorescein Labelling of Grb2-SH2

In this example the recombinant C-terminal hydrazide derivative of Grb2-SH2, generated through hydrazine cleavage of the precursor intein fusion protein, was reacted with a ketone containing derivative of fluorescein to afford site-specific fluorescent labelling of the protein.

To facilitate fluorescent labelling of C-terminal hydrazide recombinant proteins using the described approach, the fluorophore needs to contain the appropriate reactive group for ligation, namely an aldehyde or ketone functionality. To this end a derivative of fluorescein was synthesized containing a pyruvoyl moiety. Initially, Fmoc-Lys(Mtt)-OH was coupled to a rink amide resin, and the Mtt group removed using standard procedures (1% TFA, 4% triisopropylsilane in dichloromethane). 5(6)-carboxyfluorescein was then couple to the lysine ε-amino group. The Fmoc group was then removed and pyruvic acid coupled to the free α-amino group of the lysine. After cleavage from the resin, the desired fluorescein derivative [designated CH$_3$COCO-Lys(F1), see FIG. 11] was purified to >95% purity by RPHPLC and lyophilised (ESMS, expected monoisotopic mass 576.2 Da; observed monoisotopic mass 576.0 Da).

To establish the reactivity of CH$_3$COCO-Lys(F1) with C-terminal hydrazide peptides and proteins, the reaction of CH$_3$COCO-Lys(F1) with a small synthetic C-terminal hydrazide peptide SLAYG-NHNH$_2$ (SEQ ID NO:5-NHNH$_2$) was investigated. A sample of CH$_3$COCO-Lys(F1) and SLAYG-NHNH$_2$ peptide were co-dissolved in 100 mM sodium acetate buffer pH 4.5 to give final concentrations of 0.3 mM and 2 mM respectively. After 20 h incubation at room temperature, the reaction was deemed complete as determined by RPHPLC analysis. All the starting CH$_3$COCO-Lys (F1) had reacted to give predominantly a single product. The mass of which corresponds to the desired ligation product, namely conjugation of the two reactants via hydrazone bond formation (ESMS expected monoisotopic mass 1079 Da; observed mass 1080 Da).

Having established the specific reaction of CH$_3$COCO-Lys (F1) with hydrazide containing peptides, this fluorescein derivative was used for the site-specific labeling of recombinant Grb2 SH2 C-terminal hydrazide (generated through hydrazine cleavage of Grb2 SH2-GyrA-CBD).

Two complementary methods were employed for the purification of Grb2 SH2 C-terminal hydrazide from the fusion protein cleavage reaction (Example 2). The purified protein was isolated as either a lyophilized solid or in a solution of 50 mM sodium acetate buffer pH 4.5. This latter buffer system was chosen as the pH is suited to hydrazone bond forming reactions. An aliquot of Grb2 SH2 C-terminal hydrazide in 50 mM sodium acetate pH 4.5 (250 μg, 200 μL) was added directly to a sample of CH$_3$COCO-Lys (F1) to give a final concentration of fluorphore of circa 0.3 mM. The reaction was incubated at room temperature and monitored by SDS-PAGE. As a control CH$_3$COCO-Lys(F1) was also incubated under the same conditions with Cytochrome C, a protein of similar same size to Grb2-SH2 but absent of a hydrazide functionality.

SDS-PAGE analysis shows that CH$_3$COCO-Lys(F1) has indeed ligated with Grb2-SH2 C-terminal hydrazide (FIG. 12) as indicated by the conversion of Grb2-SH2 C-terminal hydrazide into a single protein species with an apparent increase in molecular weight (approximately 1000-2000 Da higher). After SDS-PAGE analysis of the reactions, fluorescence imaging of the gel confirmed that the newly formed reaction product contains a fluorescein label, and that the reaction is clean, with only a single fluorescent protein product being formed (FIG. 14). The reaction is virtually complete after 24 h and the reaction product appears to be stable under these conditions.

On the other hand there was no observable change to Cytochrome C over the time course of the experiment i.e no ligation (FIG. 13) with a complete absence of the formation of any fluorescent protein products (FIG. 14). Thus establishing that the ligation reaction is occurring at the C-terminal hydrazide functionality of Grb2 SH2, to yield site-specific C-terminal fluorescent labelling of the recombinant protein.

After 48 h of reaction, the product from the ligation reaction with Grb2 SH2 was isolated by HPLC. The mass of this product, by ESMS, confirmed the addition of one fluorescein group to the protein.

In another example, lyophilised Grb2 SH2 C-terminal hydrazide was directly dissolved into 100 mM sodium acetate pH 4.5 and added to $CH_3COCO$-Lys(F1). Whilst some protein precipitation was observed, the soluble fraction of the protein reacted with $CH_3COCO$-Lys (F1) in the anticipated manner described above.

In an alternative strategy, a lyophilized sample of Grb2 SH2 C-terminal hydrazide (250 µg) was dissolved in 40% aqueous acetonitrile containing 0.1% TFA (200 µL). This solution was then added to a sample of $CH_3COCO$-Lys(F1) to give a final fluorophore concentration of circa 0.3 mM. The solution was incubated at room temperature and the reaction periodically analyzed. SDS-PAGE analysis showed that the labeling reaction had occurred cleanly and rapidly under these conditions (FIG. 15). Grb2 SH2 C-terminal hydrazide was converted into a single protein species with an apparent increased molecular weight expected for that of the desired product, and this newly formed protein was green fluorescent when visualised under a UV lamp. ESMS of the reaction product confirmed that one fluoresein molecule had been added to the protein. The reaction is virtually complete after 4 h, with prolonged incubation appearing to be detrimental to the formation of the ligation product.

Example 6

Ligation of Aldehyde and Ketone Containing Peptides and Labels to Recombinant C-Terminal Hydrazide Containing Proteins: Fluorescein Labelling of MBP As a further exemplification, the described approach was used for the site-specific C-terminal labeling of MBP with fluorescein. A sample (250 µg) of lyophilised recombinant MBP C-terminal hydrazide (generated through hydrazine cleavage of MBP-VMA-CBD precursor fusion protein) was dissolved in 40% aqueous acetonitrile containing 0.1% TFA (200 µL). The solution was then added to a sample of $CH_3COCO$-Lys (F1) to give a final fluorophore concentration of circa 0.3 mM. The reaction was then incubated at room temperature and periodically analyzed by SDS-PAGE.

SDS-PAGE analysis showed that the fluorescein labelling reaction had occurred under these conditions, as indicated by the formation of a single green fluorescent species with a molecular weight of circa 42 KDa. MALDI analysis of the reaction mixture after 48 h was consistent with the addition of one fluorescein molecule to MBP.

In summary, the present invention provides novel methods of protein ligation and protein labelling. These enable both synthetic and recombinantly derived protein fragments to be efficiently joined together in a regioselective manner. This thus enables large proteins to be constructed from combinations of synthetic and recombinant fragments and allows proteins of any size to be site-specifically modified in an unprecedented manner. This is of major importance for biological and biomedical science and drug discovery when one considers that the ~30,000 human genes yield hundreds of thousands of different protein species through post-translational modification. Such post-translationally modified proteins cannot be accessed through current recombinant technologies.

The application of such protein ligation techniques may be used for protein based tools, protein therapeutics and in de novo design and may open up many new avenues in biological and biomedical sciences that have hitherto not been possible.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

SEQUENCE LISTING

```
<160> NUMBER OF SEQ ID NOS: 6

<210> SEQ ID NO 1
<211> LENGTH: 27
<212> TYPE: PRT
<213> ORGANISM: Artificial sequence
<220> FEATURE:
<223> OTHER INFORMATION: Synthetic C-terminal thioester peptide
<220> FEATURE:
<221> NAME/KEY: misc_feature
<222> LOCATION: (1)..(1)
<223> OTHER INFORMATION: Xaa may be alanine or arginine
<220> FEATURE:
<221> NAME/KEY: misc_feature
<222> LOCATION: (7)..(7)
<223> OTHER INFORMATION: Xaa may be alanine or arginine
<220> FEATURE:
<221> NAME/KEY: misc_feature
<222> LOCATION: (9)..(9)
<223> OTHER INFORMATION: (Me)3
<220> FEATURE:
<221> NAME/KEY: misc_feature
<222> LOCATION: (15)..(15)
<223> OTHER INFORMATION: Xaa may be alanine or arginine
<220> FEATURE:
```

-continued

```
<221> NAME/KEY: misc_feature
<222> LOCATION: (21)..(21)
<223> OTHER INFORMATION: Xaa may be alanine or arginine
<220> FEATURE:
<221> NAME/KEY: misc_feature
<222> LOCATION: (24)..(24)
<223> OTHER INFORMATION: Xaa may be alanine or arginine
<220> FEATURE:
<221> NAME/KEY: misc_feature
<222> LOCATION: (25)..(25)
<223> OTHER INFORMATION: Xaa may be alanine or arginine

<400> SEQUENCE: 1

Xaa Arg Thr Lys Gln Thr Xaa Arg Lys Ser Thr Gly Gly Lys Xaa Pro
1               5                   10                  15

Arg Lys Gln Leu Xaa Thr Lys Xaa Xaa Arg Lys
            20                  25

<210> SEQ ID NO 2
<211> LENGTH: 102
<212> TYPE: PRT
<213> ORGANISM: Homo sapiens

<400> SEQUENCE: 2

His Pro Trp Phe Phe Gly Lys Ile Pro Arg Ala Lys Ala Glu Glu Met
1               5                   10                  15

Leu Ser Lys Gln Arg His Asp Gly Ala Phe Leu Ile Arg Glu Ser Glu
            20                  25                  30

Ser Ala Pro Gly Asp Phe Ser Leu Ser Val Lys Phe Gly Asn Asp Val
        35                  40                  45

Gln His Phe Lys Val Leu Arg Asp Gly Ala Gly Lys Tyr Phe Leu Trp
    50                  55                  60

Val Val Lys Phe Asn Ser Leu Asn Glu Leu Val Asp Tyr His Arg Ser
65                  70                  75                  80

Thr Ser Val Ser Arg Asn Gln Gln Ile Phe Leu Arg Asp Ile Glu Gln
                85                  90                  95

Val Pro Gln Gln Pro Thr
            100

<210> SEQ ID NO 3
<211> LENGTH: 36
<212> TYPE: PRT
<213> ORGANISM: Artificial sequence
<220> FEATURE:
<223> OTHER INFORMATION: Purified and lyophilised Grb2-SH2 C terminal
      hydrazide treated with protease Lys-C in 100mM ammonium
      bicarbonate buffer

<400> SEQUENCE: 3

Phe Asn Ser Leu Asn Glu Leu Val Asp Tyr His Arg Ser Thr Ser Val
1               5                   10                  15

Ser Arg Asn Gln Gln Ile Phe Leu Arg Asp Ile Glu Gln Val Pro Gln
            20                  25                  30

Gln Pro Thr Gly
        35

<210> SEQ ID NO 4
<211> LENGTH: 392
<212> TYPE: PRT
<213> ORGANISM: Homo sapiens

<400> SEQUENCE: 4

Met Lys Ile Glu Glu Gly Lys Leu Val Ile Trp Ile Asn Gly Asp Lys
```

-continued

```
1               5               10              15

Gly Tyr Asn Gly Leu Ala Glu Val Gly Lys Lys Phe Glu Lys Asp Thr
            20                  25              30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
            50                  55                  60

His Asp Arg Phe Gly Gly Tyr Ala Gln Ser Gly Leu Leu Ala Glu Ile
65                      70                  75                  80

Thr Pro Asp Lys Ala Phe Gln Asp Lys Leu Tyr Pro Phe Thr Trp Asp
                    85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
                115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
            290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
            370                 375                 380

Glu Gly Arg Gly Thr Leu Glu Gly
385                 390
```

```
<210> SEQ ID NO 5
<211> LENGTH: 5
<212> TYPE: PRT
<213> ORGANISM: Artificial sequence
<220> FEATURE:
<223> OTHER INFORMATION: Small synthetic C-terminal hydrazide peptide

<400> SEQUENCE: 5

Ser Leu Ala Tyr Gly
1               5

<210> SEQ ID NO 6
<211> LENGTH: 11
<212> TYPE: PRT
<213> ORGANISM: Artificial sequence
<220> FEATURE:
<223> OTHER INFORMATION: Synthetic peptide corresponding to the c-myc
      epitope sequence was synthesised GEQKLISEED-NH2 whereby pyruvic
      acid was coupled to the amino terminus of the peptide as the last
      step of the assembly
<220> FEATURE:
<221> NAME/KEY: MOD_RES
<222> LOCATION: (11)..(11)
<223> OTHER INFORMATION: AMIDATION

<400> SEQUENCE: 6

Gly Glu Gln Lys Leu Ile Ser Glu Glu Asp Leu
1               5                   10
```

The invention claimed is:

1. A method of producing an oligopeptide product, the method comprising the steps:
   a) providing a first oligopeptide, the first oligopeptide having a reactive moiety,
   b) providing a second oligopeptide, the second oligopeptide having an activated ester moiety, and
   c) allowing the reactive moiety of the first oligopeptide to react with the activated ester moiety of the second oligopeptide to form an oligopeptide product, in which the first and second oligopeptides are linked via a linking moiety having Formula I or Formula III:

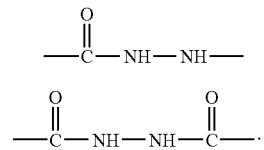

2. A method of producing an oligopeptide product, the method comprising the steps:
   a) providing a first oligopeptide, the first oligopeptide having a reactive moiety,
   b) providing a second oligopeptide, the second oligopeptide having an activated ester moiety, and
   c) allowing the reactive moiety of the first oligopeptide to react with the activated ester moiety of the second oligopeptide to form an oligopeptide product, in which the first and second oligopeptides are linked via a linking moiety having Formula I, Formula II or Formula III:

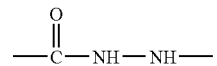 Formula I

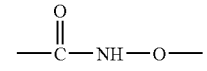 Formula II

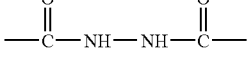 Formula III wherein the activated ester moiety is a thioester moiety wherein the second oligopeptide is the acyl substituent of the thioester moiety.

3. The method according to claim 2, wherein said second oligopeptide having said thioester moiety is generated by thiol reagent dependent cleavage of a precursor molecule, said precursor molecule comprising the second oligopeptide fused N-terminally to an intein domain.

4. A method of producing an oligopeptide product, the method comprising the steps:
   a) providing a first oligopeptide, the first oligopeptide having a reactive moiety,
   b) i) providing a precursor oligopeptide molecule, the precursor oligopeptide molecule comprising a polypeptide fused N-terminally to an intein domain,
   ii) allowing thiol reagent dependent cleavage of the precursor oligopeptide molecule to generate a second oligopeptide molecule, said second oligopeptide molecule having a thioester moiety at its C-terminus, and
   c) allowing the reactive moiety of the first oligopeptide to react with the second oligopeptide molecule to form an oligopeptide product, in which the first oligopeptide and the second oligopeptide molecule are linked via a linking moiety having Formula I, II or III:

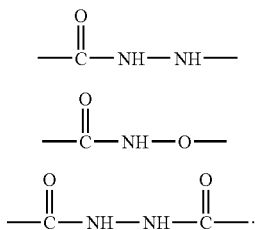

5. The method according claim 1 wherein the reactive moiety is a hydrazine moiety or a hydrazide moiety.

6. A method of producing an oligopeptide product, the method comprising the steps:
  a) providing a first oligopeptide, the first oligopeptide having a reactive moiety,
  b) providing a second oligopeptide, the second oligopeptide having an activated ester moiety, and
  c) allowing the reactive moiety of the first oligopeptide to react with the activated ester moiety of the second oligopeptide to form an oligopeptide product, in which the first and second oligopeptides are linked via a linking moiety having Formula II:

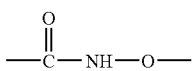

Formula II wherein the reactive moiety is an aminooxy moiety and the activated ester moiety is a thioester moiety.

7. A method of producing an oligopeptide product, the method comprising the steps:
  a) providing a first oligopeptide, the first oligopeptide having a reactive moiety.
  b) providing a second oligopeptide, the second oligopeptide having an activated ester moiety, and
  c) allowing the reactive moiety of the first oligopeptide to react with the activated ester moiety of the second oligopeptide to form an oligopeptide product, in which the first and second oligopeptides are linked via a linking moiety having Formula III:

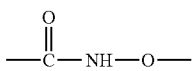

Formula II wherein said reactive moiety is a hydrazide moiety and wherein said first oligopeptide is produced by reaction of hydrazine with a precursor molecule, said precursor molecule comprising a precursor oligopeptide fused N-terminally to an intein domain via a thioester moiety.

8. A method of producing an oligopeptide product, said method comprising the steps:
  a) providing a first oligopeptide, the first oligopeptide having a reactive moiety, wherein the reactive moiety is a hydrazine moiety, a hydrazide moiety or an amino-oxy moiety;
  b) providing a precursor oligopeptide molecule, the precursor oligopeptide molecule comprising a second oligopeptide fused N-terminally to an intein domain; and
  c) allowing the reactive moiety of the first oligopeptide to react with the precursor oligopeptide molecule to form an oligopeptide product, in which the first and second oligopeptides are linked via a linking moiety having Formula I, Formula II or Formula III:

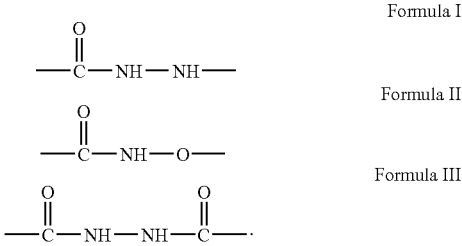

9. The method according to claim 1 or 8, wherein the first oligopeptide or the second oligopeptide is a recombinant oligopeptide and the other of the first oligopeptide and the second oligopeptide is a synthetic oligopeptide.

10. The method according to claim 1 or 8, wherein the first oligopeptide and the second oligopeptide are recombinant oligopeptides.

11. The method according to claim 1 or 8, wherein the first oligopeptide and the second oligopeptide are synthetic oligopeptides.

12. A method of generating a protein hydrazide, said method comprising the steps:
  (a) providing a protein molecule comprising an oligopeptide fused N-terminally to an intein domain, and
  (b) reacting said protein molecule with hydrazine, such that the intein domain is cleaved from the oligopeptide to generate a protein hydrazide.

13. The method according to claim 1 wherein step (c) of the method is performed at a pH in the range pH 6.5 to 7.5.

14. A method of producing an oligopeptide product, the method comprising the steps:
  a) providing a first oligopeptide, the first oligopeptide having an aldehyde or ketone moiety,
  b) providing a precursor oligopeptide molecule, the precursor oligopeptide molecule comprising a second oligopeptide fused N-terminally to an intein domain,
  c) reacting said precursor oligopeptide molecule with hydrazine to generate an intermediate oligopeptide, said intermediate oligopeptide having a terminal hydrazide moiety, and
  d) allowing the aldehyde or ketone moiety of the first oligopeptide to react with the hydrazide moiety of the intermediate oligopeptide to form an oligopeptide product, in which the first oligopeptide and the second oligopeptide are linked via a hydrazone linking moiety.

15. A method of labelling an oligopeptide, the method comprising the steps:
  a) providing a label molecule, the label molecule having an activated ester moiety of which the label is the acyl substituent,
  b) providing the oligopeptide, the oligopeptide having a reactive moiety, and
  c) allowing the activated ester moiety of the label molecule to react with the reactive moiety of the oligopeptide to form a labelled oligopeptide, in which the label molecule and the oligopeptide are linked via a linking moiety having Formula III:

Formula III

16. The method according to claim 15 wherein said oligopeptide is produced by reaction of hydrazine with a precursor molecule, said precursor molecule comprising a precursor oligopeptide fused N-terminally to an intein domain via a thioester moiety.

17. A method of labelling an oligopeptide, the method comprising the steps:
   a) providing a label, the label having a reactive moiety,
   b)(i) providing a precursor oligopeptide molecule, the precursor oligopeptide molecule comprising an oligopeptide fused N-terminally to an intein domain,
   (ii) allowing thiol reagent dependent cleavage of the precursor oligopeptide molecule to generate said oligopeptide, said oligopeptide having a thioester moiety at its C-terminus, and
   c) allowing the reactive moiety of the label to react with the oligopeptide of step (b)(ii) to form a labelled oligopeptide, in which the label and said oligopeptide are linked via a linking moiety having Formula III:

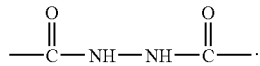

Formula III

18. A method of labelling an oligopeptide, the method comprising the steps:
   a) providing a label molecule, the label molecule having a reactive moiety,
   b) providing a precursor oligopeptide molecule, the precursor oligopeptide molecule comprising an oligopeptide fused N-terminally to an intein domain, and
   c) allowing the reactive moiety of the label molecule to react with the precursor oligopeptide molecule to form a labelled oligopeptide product, in which the label molecule and the oligopeptide are linked via a linking moiety having Formula I, Formula II or Formula III:

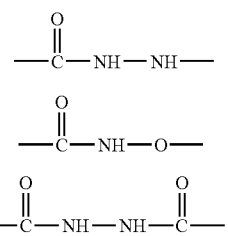

Formula I

Formula II

Formula III

19. A method of labelling an oligopeptide to produce a labelled oligopeptide product, the method comprising the steps:
   a) providing a label molecule, the label molecule having an aldehyde or ketone moiety,
   b) providing a precursor oligopeptide molecule, the precursor oligopeptide molecule comprising a first oligopeptide fused N-terminally to an intein domain,
   c) reacting said precursor oligopeptide molecule with hydrazine to generate an intermediate oligopeptide molecule, said intermediate oligopeptide molecule having a terminal hydrazide moiety, and
   d) allowing the aldehyde or ketone moiety of the label molecule to react with the hydrazide moiety of the intermediate oligopeptide molecule to form a labelled oligopeptide product, in which the label molecule and oligopeptide are linked via a hydrazone linking moiety.

20. The method according to claim 14 or claim 19, wherein the aldehyde or ketone moiety is an α-diketone or an α-ketoaldehyde group.

* * * * *

UNITED STATES PATENT AND TRADEMARK OFFICE
CERTIFICATE OF CORRECTION

PATENT NO. : 7,622,552 B2  Page 1 of 1
APPLICATION NO. : 10/567403
DATED : November 24, 2009
INVENTOR(S) : Graham Cotton It is certified that error appears in the above-identified patent and that said Letters Patent is hereby corrected as shown below:

Column 29, lines 51-55, "Formula II" should read --Formula III--, and the chemical structure " 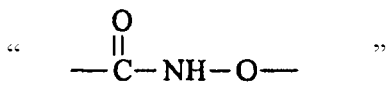 "

should read

--  --.

Signed and Sealed this

Twenty-third Day of February, 2010

David J. Kappos
*Director of the United States Patent and Trademark Office*